US008410170B2

(12) United States Patent
Cheng et al.

(10) Patent No.: US 8,410,170 B2
(45) Date of Patent: Apr. 2, 2013

(54) USE OF ISOTHIOCYANATES COMPOUNDS IN TREATING PROSTATIC DISEASES AND SKIN CANCER

(75) Inventors: Jingcai Cheng, Wuxi (CN); Jenwei Chiao, Wuxi (CN); Haiya Jin, Wuxi (CN); Chengjuan Zhong, Wuxi (CN)

(73) Assignee: Wuxi JC Pharmaceutical Technology Co., Ltd., Wuxi, Jiangsu (CN)

( * ) Notice: Subject to any disclaimer, the term of this patent is extended or adjusted under 35 U.S.C. 154(b) by 0 days.

(21) Appl. No.: 13/231,406

(22) Filed: Sep. 13, 2011

(65) Prior Publication Data

US 2012/0046358 A1 Feb. 23, 2012

Related U.S. Application Data

(62) Division of application No. 12/093,829, filed as application No. PCT/CN2006/003062 on Nov. 14, 2006, now Pat. No. 8,039,511.

(30) Foreign Application Priority Data

Nov. 15, 2005 (CN) .......................... 2005 1 0095737
Jan. 27, 2006 (CN) .......................... 2006 1 0038112

(51) Int. Cl.
*A61K 31/26* (2006.01)
(52) U.S. Cl. .......................... 514/514; 514/649; 514/665
(58) Field of Classification Search ........................ None
See application file for complete search history.

(56) References Cited

U.S. PATENT DOCUMENTS

2005/0070602 A1 3/2005 Chiao et al.
2006/0069151 A1 3/2006 Barella et al.
2010/0204319 A1 8/2010 Archibald

FOREIGN PATENT DOCUMENTS

CN 1724516 1/2006

OTHER PUBLICATIONS

Wikipedia contributors, "Methyl isocyanate," Wikipedia, The Free Encyclopedia, http://en.wikipedia.org/w/index.php?title=Methyl_isocyanate&oldid=505030922 (accessed Aug. 17, 2012), 6 pages total.
European Search Report issued Mar. 19, 2012 in corresponding European patent application No. 11186589, 9 pages total.
Hecht et al. "Inhibition of lung tumorigenesis in A/J mice by N-acetyl-S-(N-2-phenethylthiocarbamol)-L-cysteine and myo-inositol, individually and in combination." Carcinogenesis, 23(9), 2002, p. 1455-1461.
Brooks et al. "Potent Induction of Phase 2 Enzymes in Human Prostate Cells by Sulforaphane." Cancer Epidemiology, Biomarkers & Prevention, 10, 2001, p. 949-954.
Ye et al., "Total intracellular accumulation levels of dietary isothiocyanates determine their activity in elevation of cellular glutathione and induction of Phase 2 detoxification enzymes." Carcinogenesis, 22(12), 2001, p. 1987-1992.
English Translation of the Written Opinion of the International Searching Authority of PCT/CN2006/003062, dated Mar. 15, 2007.
English Translation of the International Preliminary Report on Patentability of PCT/CN2006/003062, report completed Mar. 6, 2008.
Wu et al. "An Experimental Study(II) on the Inhibition of Prostatic Hyperplasia by Extract of Seeds of *Brassica alba*." China Journal of Chinese Materia Medica, vol. 28(7), Jul. 2003, pp. 643-646.
Ou et al. "A Brief Review on the Study of Seeds of *Brassica alba*." Strait Pharmaceutical Journal, vol. 13(2), 2001, pp. 8-11.
Supplementary European Search Report issued Jul. 31, 2009 by the European Patent Office in Application No. EP 06 81 78015.
Chen et al. "Phenylethyl Isothiocyanate Induces Apoptotic Signaling via Suppressing Phosphatase Activity against c-Jun N-terminal Kinase." Journal of Biological Chemistry, vol. 277 No. 42, Oct. 18, 2002, pp. 39334-39342.
Srivastava et al. "Allyl isothiocyanate, a constituent of cruciferous vegetables, inhibits growth of PC-3 human prostate cancer xenografts in vivo." Carcinogenesis, vol. 24 No. 10, Oct. 2003, pp. 1665-1670.
Zuniga et al. "Isothiocyanates inhibit cell growth and induce apoptosis in prostate cancer cells derived from TRAMP mice." Proceedings of the American Association for Cancer Research Annual Meeting, vol. 43, Mar. 2002, p. 640.
Myzak et al. "Sulforaphane inhibits histone deacetylase activity in BPH-1, LnCaP and PC-3 prostate epithelial cells." Carcinogenesis col. 27 No. 4, Apr. 2006, pp. 811-819.
Wang et al. "Repression of androgen receptor in prostate cancer cells by phenethyl isothiocanante," Carcinogenesis, vol. 27 No. 10, Oct. 2006, pp. 2124-2132.
Office Action issued Apr. 8, 2010 in corresponding European Patent Application No. 06817815.1 (6 pages).
Office Action issued Mar. 8, 2010 in corresponding Canadian Patent Application No. 2630262 (4 pages).
Office Action Issued for EP Patent Application No. 06 817 815.1-2123, dated Oct. 14, 2010 (5 pages).
International Search Report for International Application No. PCT/CN2006/003062 and English translation thereof, dated Mar. 15, 2007, 11 pages total.
Saracoglu et al., "Broccoli Kur für Prostatitis und BPH Patienten", Duetsches Medizin Forum, http://web.archive.org/web/20050306131255/http://www.medizin-forume.de/prostatitis/broccoli-d.html, accessed Feb. 8, 2012 (and European Search Report issued Mar. 19, 2012 in corresponding European patent application No. 11186579), 11 pages total.

*Primary Examiner* — James D Anderson
(74) *Attorney, Agent, or Firm* — Hamre, Schumann, Mueller & Larson, P.C.

(57) ABSTRACT

A method for preventing and treating prostatic diseases and skin cancer using naturally or artificially synthesized isothiocyanates compounds or the derivatives or metabolites thereof.

12 Claims, 6 Drawing Sheets

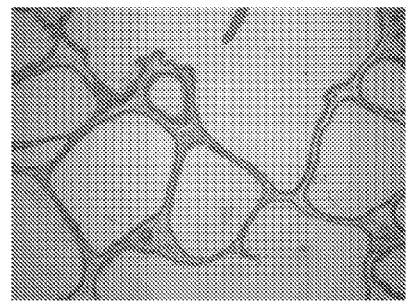
Figure 5
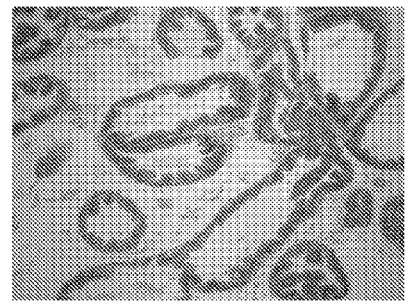
Figure 6.1
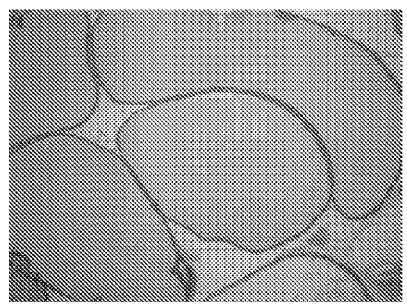
Figure 6.2
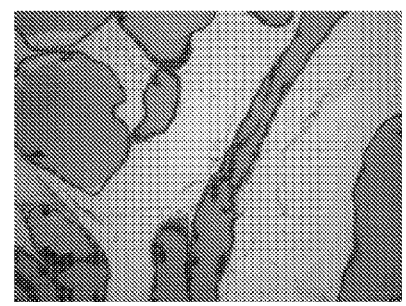
Figure 6.3
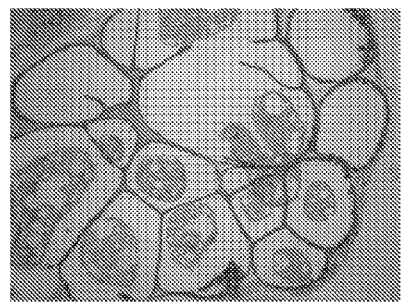
Figure 6.4
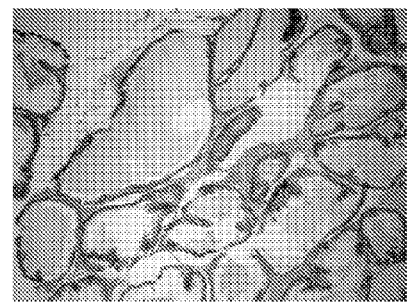
Figure 6.5

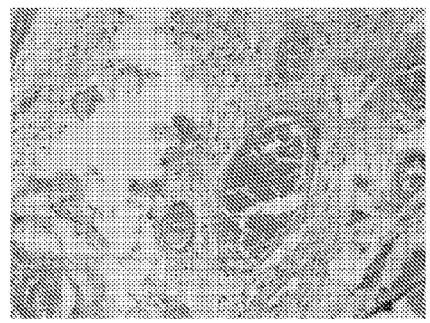
Figure 7.1
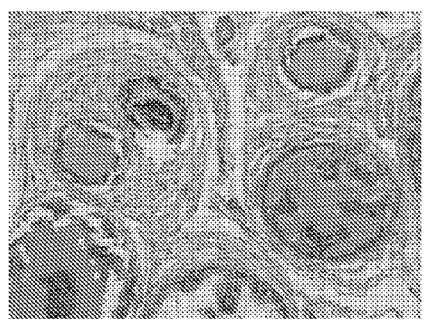
Figure 7.2
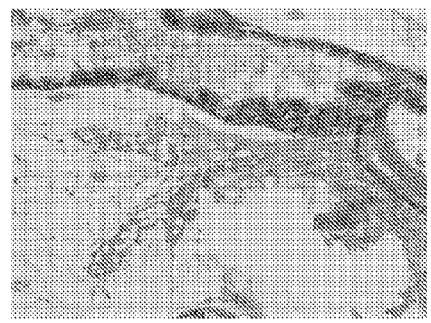
Figure 7.3
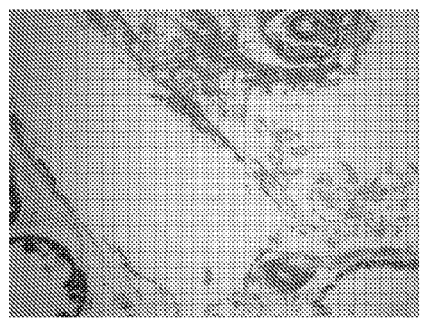
Figure 7.4
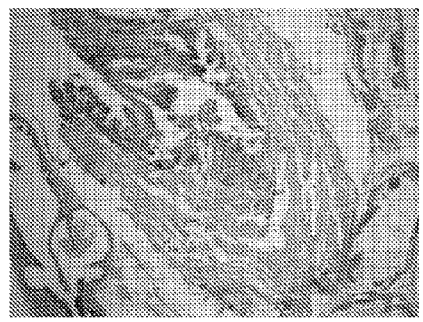
Figure 7.5

USE OF ISOTHIOCYANATES COMPOUNDS IN TREATING PROSTATIC DISEASES AND SKIN CANCER

TECHNICAL FIELD

The invention relates to the application of isothiocyanates or their derivatives or their metabolites, no matter nature or synthesis, in the treatment and prevention of benign prostatic hyperplasia (BPH), prostatitis and melanoma.

BACKGROUND

Prostate gland enlargement or benign prostatic hyperplasia (BPH) is a common disease in aging men. Besides the age, the loss of Phase II detoxification enzyme, i.e. glutathione S-transferase (GSTP1) gene, and abnormal of androgen are believed to be involved in the development of the disease. The incidence of BPH is quite low in men under age 40, about 40% in men at age 50, and it almost reaches 90% at age 80, nearly 100% histochemically in men at age of 90 years old. Among them about 25% of patients need treatments either by surgery or medicine, or both, due to severe blockage of urinary tract. Obviously, numbers of patients with BPH will significantly increase as a result of the quickening life style and longer life span. Moreover, recent studies indicate that more BPH occurs in younger men.

Prostate is consisting of glands and muscles. In those tissues, phase II detoxification enzymes are often chronically inactivated with aging by unknown epigenetic reasons. Thus, the ability of cells to defense invasion of toxic materials from environment is decreased. As a result, prostate cells are inflammated or extra proliferation of noninflammated tissue, thereby becoming prostatitis or benign prostatic hyperplasia. Patients with BPH often suffer from urinary difficulty, due to the urethra squeezed by the enlarged prostate. If left untreated and unmonitored, BPH may lead to serious complications, such as frequent urination, urination difficulty, acute urina retention, urinary tract infection, bladder stone, rectal prolapse, internal hemorrhoids, sexual dysfunction, high blood pressure, heart attack, stroke, urinemia or even prostate cancer.

The current clinical available pharmaceutical products of BPH can be classified into three categories: 5-alpha-reductase inhibitors, alpha(1)-receptor antagonists, and natural herbal medicine—Hua Fen. Among them, the Proscar, a 5-alpha reductase inhibitor, manufactured by Merck & Co. Inc, is mainly used for the treatment of BPH. However, clinical studies indicate that Proscar is effective only for patients with relatively large volume (>40 cm$^3$) of the prostate; otherwise the efficacy is not satisfactory. Since alpha(1)-receptor antagonists exhibit their activities by relaxation of muscles of bladder neck and tissues surrounding the prostate, it can only relieves symptoms, but not reduce volume of the enlarged prostate.

Prostatitis is another common disease in men of any age, and it is the most common in young and middle-aged men. Prostatitis can be classified as two types: acute, bacterial infected inflammation and chronic, non-bacterial infected inflammation. Major symptoms of prostatitis include urinating pain, milky urine, urinary fever, frequent urination, pain in lower abdomen; even worse, symptoms like fever or chills. Sometimes symptoms of prostatitis are similar to those of BPH. In this invention, we used GENURIN® (Flavoxate Hydrochloride) as positive control for the treatment of prostatitis. This drug is invented and manufactured by the Lifephama S.r.l, Italy, after its research for many years. GENURIN® is indicated to treat bladder and protatic diseases: symptoms like urinary difficulty, urinary urgency, night urine, pain in haunch bone etc. caused by cystitis and bladder pain, prostatitis, urethritis, bladder urethritis etc. Clinical studies have shown that this drug is rapidly absorbed after orally administration, and distribute into various tissues/organs, and eliminated from urine. It selectively acts on smooth muscles of genitourinary system, thereby relieves bladder symptoms caused by irritations.

Incidence of skin cancer is relatively low in Chinese, however it is a common malignancy in Caucasians. Skin cancer may occur in any part of the body, about 80% occur in the skin of the face, head, neck and induce abnormality and danger. UV light, mostly coming from the sun, is a major factor to cause skin cancer, thus theoretically, there are no differences in incidence of skin cancer between races, skin categories, ages, occupations and locations. Everyone has the possibility to suffer from skin cancer. Currently, there are not many available drugs for the treatment of skin cancer. However patients with skin cancer are increasing year by year based on related media. A report from WHO in July 2006 indicated that there were 60,000 people died, mostly suffering from skin cancer, due to overexposure to sunlight every year. Among them 48,000 cases were melanoma, and 12,000 cases were other types of skin cancer. Thus, development of new types of pharmaceutical products and dietary supplements to prevent and/or treat skin cancer is highly warranted.

In summary, prostate diseases are major diseases to affect men health. These diseases will seriously impact our society which is turning into an aged society. At the same time, more and more patients are suffering from skin cancer. Innovative and effective pharmaceutical products or dietary supplements, food, cosmetics to treat and/or prevent those disorders are, therefore, very much needed.

DETAILED DESCRIPTION OF THE PREFERRED EMBODIMENTS

This invention relates to the application of the natural or synthetic isothiocyanates or their derivatives or their metabolites. The invention further relates to the formulations and the preparation methods of the formulations of natural or synthetic isothiocyanates or their derivatives or their metabolites.

One purpose of this invention is to use the isothiocyanates or their derivatives or their metabolites to treat and/or prevent the diseases such as benign prostatic hyperplasia (BPH), prostatitis and skin cancer etc.

The secondary purpose of this invention is to use the isothiocyanates or their derivatives or their metabolites as active pharmaceutical ingredients (API) to prepare formulations suitable for treatment and/or prevention of the diseases such as benign prostatic hyperplasia (BPH), prostatitis and skin cancer etc.

The third purpose of this invention is to provide preparation methods of formulations using the isothiocyanates or their derivatives or their metabolites as active pharmaceutical ingredients.

This invention relates the natural and synthetic isothiocyanates which include, but not limited to benzyl isothiocyanate (BITC), phenethyl isothiocyanate (PEITC), allyl isothiocyanate (AITC) and 4-sulfophenylisothiocyanate (SPITC), their chemical structures are listed below as (1), (2), (3), and (4), respectively:

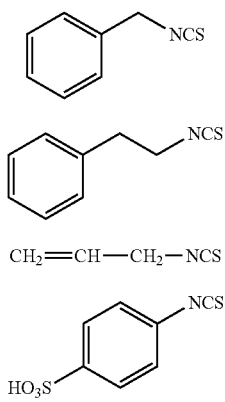

(1), (2), (3), (4)

This invention relates to the derivatives and metabolites of isothiocyanates. These compounds include, but not limited to isothiocyanate conjugates, including glutathione-, cysteinyl glycine-, cysteinyl-, and N-acetylcysteine-. The preferred conjugate is N-acetylcysteine (NAC) conjugate.

This invention relates to the derivatives and metabolites of isothiocyanates. These compounds include, but not limited to N-acetylcysteine conjugate of benzyl isothiocyanate (BITC-NAC), N-acetylcysteine conjugate of phenethyl isothiocyanate (PEITC-NAC), N-acetylcysteine conjugate of allyl isothiocyanate (AITC-NAC), and N-acetylcysteine conjugate of 4-sulfophenylisothiocyanate (SPITC-NAC). Their chemical structures are listed below as (5), (6), (7), and (8), respectively:

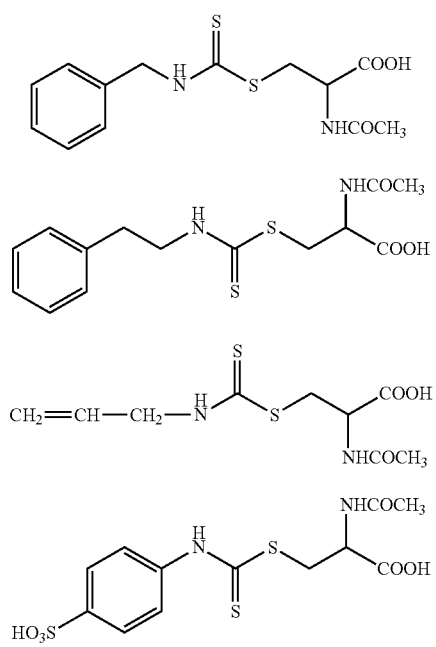

(5), (6), (7), (8)

The isothiocyanates or their derivatives or their metabolites demonstrated in this invention are used for the prevention and treatment of diseases of the prostate and skin cancer. The compounds shown the good efficacy are phenethyl isothiocyanate (PEITC), benzyl isothiocyanate (BITC) and their N-acetylcysteine conjugates. The compounds shown the better efficacy are phenethyl isothiocyanate (PEITC) and N-acetylcysteine conjugate of phenethyl isothiocyanate (PEITC-NAC). The compound shown the best efficacy is phenethyl isothiocyanate (PEITC).

The isothiocyanates or their derivatives or their metabolites involved in this invention are used for the treatment and/or prevention of diseases of the prostate and skin cancer. The preferred diseases of the prostate are benign prostatic hyperplasia (BPH) and prostatitis, particularly the benign prostatic hyperplasia.

The isothiocyanates or their derivatives or their metabolites involved in this invention include, but not limited to phenethyl isothiocyanate (PEITC), benzyl isothiocyanate (BITC), allyl isothiocyanate (AITC), 4-sulfophenylisothiocyanate (SPITC) and N-acetylcysteine conjugate of phenethyl isothiocyanate (PEITC-NAC). All of those compounds are able to effectively induce expressions of phase II detoxification enzyme, i.e. glutathione S-transferase (GSTP1) gene, enable prostate cells to eliminate invasions of toxic materials. Therefore, those compounds are able to effectively treat and/or prevent inflammations and other related diseases of the prostate and other tissues/organs.

The isothiocyanates or their derivatives or their metabolites involved in this invention include, but not limited to phenethyl isothiocyanate (PEITC), benzyl isothiocyanate (BITC), allyl isothiocyanate (AITC) and N-acetylcysteine conjugate of phenethyl isothiocyanate (PEITC-NAC). Those compounds effectively repress expressions of the androgen receptor (AR), transcription factor Sp1, an upstream gene of AR, and prostate specific antigen (PSA), a downstream gene of the AR.

Compositions containing one or more active pharmaceutical ingredients (API) described in this invention can be used as pharmaceutical products, food, dietary supplements, or cosmetics.

Compositions described in this invention contain one or more of the isothiocyanates or their derivatives or their metabolites as API together with other ingredients listed below:

(a) 0.5-50 portion (w/w) of API, which includes isothiocyanates and/or their derivatives, their metabolites. The isothiocyanates include, but not limited to phenethyl isothiocyanate (PEITC), benzyl isothiocyanate (BITC), allyl isothiocyanate (AITC), 4-sulfophenylisothiocyanate (SPITC). The derivatives herein include, but not limited to isothiocyanate conjugates of N-acetylcysteine. The preferred compounds are N-acetylcysteine conjugate of phenethyl isothiocyanate (PEITC-NAC), N-acetylcysteine conjugate of benzyl isothiocyanate (BITC-NAC), N-acetylcysteine conjugate of allyl isothiocyanate (AITC-NAC), and N-acetylcysteine conjugate of 4-sulfophenylisothiocyanate (SPITC-NAC).

(b) 0 to 1000 portion (w/w) of API pharmaceutical carrier, the pharmaceutical carrier include:

(b1) 0 to 1000 portion (w/w) of pharmaceutical surfactants or solubilizing agents, the described surfactants were selected from: polyoxyethylene lauryl ether (preferentially polyoxyethylene 23 lauryl ether), polyoxyethylene glycol stearate (preferentially, Polyoxyethylene (40) monostearate), Vitamin E polyethylene glycol succinate, polyoxyethylene castor oil (preferentially, polyoxyethylene (35) castor oil), polyoxyethylene hydrogenated castor oil (preferentially, Polyoxyethylene (40) hydrogenated castor oil), poloxamer (preferentially, poloxamer-F127, poloxamer F-68), polysorbates (Tween 80) or their combination. The described solubilizing agents include: polyvinylpyrrolidone K17, K25, K30, K90, polyethylene glycol 400, 4000, and 6000 or their combination. Preferentially, the described surfactants, and solubilizing agents are polyoxyethylene (40) monostearate, polyoxyethylene 23 lauryl ether, Vitamin E polyethylene glycol succinate, polyoxyethylene (40) hydrogenated castor oil or their combination, particularly, polyoxyethylene (40) monostearate.

(b2) 0 to 500 portions (w/w) of oil components, were selected from fatty acids or triglyceride, monoglyceride or diglyceride, which include, but not limited to soybean oil, corn oil, peanut oil, stearic acid, palmitic acid, palm oil, sunflower oil, olive oil, coconut oil, sesame oil, cottonseed oil, canola oil, oleic acid, linoleic acid, medium-chain triglycerides, glyceryl monooctadecanoate, glyceryl monoacetate, glyceryl diacetate, glyceryl triacetate, or one or more than one combination. Preferentially, the described oil components were selected from: medium-chain triglycerides, triglyceride, soybean oil, corn oil, cottonseed oil, stearic acid, oleic acid, particularly: medium-chain (i.e. C8 to C12) triglycerides, soybean oil, corn oil, and the best one is medium-chain triglycerides.

(b3) 0 to 25 portions (w/w) of antioxidants are selected from: water-soluble antioxidants, fat-soluble antioxidant, such as vitamin C, vitamin C palmitate, propyl gallate, vitamin E (tocopherol), tert-butylated-p-hydroxyanisole, 2,6-di-tert-butyl-p-methylphenol, or combination of one or more than one of the above components. Preferentially, those antioxidants are vitamin C, vitamin C palmitate, propyl gallate, tert-butylated-p-hydroxyanisole, and the best choice is vitamin C palmitate.

(b4) is one or more than one of combination of (b1), (b2), and (b3).

To further prepare other suitable dosage forms, the following excipients may be added into the pharmaceutical products and dietary supplements described in this invention:

(a) Adsorbents and diluents: the adsorbents and diluents are selected from α-lactose(monohydrate), anhydrous lactose, β-cyclodextrin, hydroxypropyl-β-cyclodextrin, microcrystalline cellulose (MCC, PH101, PH102, KG series), microcrystalline cellulose pills, lactose starch pills, calcium carbonate, calcium hydrocarbonate, modified starch, sucrose octaacetate, sodium carboxymethyl starch, hydroxypropyl cellulose, stearic acid, mannitol, sorbitol, sorbic acid, sodium carboxymethyl cellulose, porous starch, colloidal silicon dioxide, or the combination of one or more than one of components described above. Preferentially, adsorbents and diluents are stearic acid, sorbitol, microcrystalline cellulose (KG series), mannitol 300 DC, β-cyclodextrin, colloidal silicon dioxide, α-lactose(monohydrate). The better ones are β-cyclodextrin, stearic acid and the best one is β-cyclodextrin. The described amount of adsorbents and diluents are between 0.5 and 1500 portions (w/w), and the better ranges are between 2.0 and 500 portions (w/w).

(b) Lubricants: The lubricants are selected from magnesium stearate, lauryl sodium sulfate, polyethylene glycol, colloidal silicon dioxide and talc. Preferentially, lubricants are magnesium stearate, polyethylene glycol and colloidal silicon dioxide. The best one is polyethylene glycol, and the ratio is between 0 and 30 portions (w/w).

(c) Binders: The binders described in this invention are selected from polyvinylpyrrolidone (PVP), hydroxypropyl cellulose, hydroxypropylmethyl cellulose, ethyl cellulose (200 mesh), polyethylene glycol (PEG). Preferentially, binders are selected from hydroxypropyl cellulose EF, PEG 6000, hydroxypropylmethyl cellulose E15. The better choices are hydroxypropylmehtyl cellulose E15, PEG 6000, and the best one is PEG 6000. The amount of the binder usually ranges between 0 and 100 portions (w/w).

(d) Disintegrating agents: The disintegrating agents described in this invention are selected from: porous starch, sodium carboxymethyl cellulose, sodium carboxymethyl starch, low-substituted hydroxypropyl cellulose, microcrystalline cellulose. The preferential selections of disintegrating agents are microcrystalline cellulose PH101, low-substituted hydroxypropyl cellulose and sodium carboxymethyl cellulose, and the best one is microcrystalline cellulose PH101. The amount of disintegrating agents is usually between 0 and 100 portions (w/w).

(e) Coating materials: The coating materials described in this invention are selected from: hydroxypropylmethyl cellulose, hydroxypropyl cellulose, methyl cellulose, ethyl cellulose, dimethylaminoethylmethylacrylate-neutral methylacrylate polymer, PEG, titanium dioxide, iron oxide red, and potassium sorbate. Among them, the described coating materials are preferentially selected from hydroxypropylmethyl cellulose E15, hydroxypropyl cellulose EF, dimethylaminoethylmethylacrylate-neutral methylacrylate polymer, PEG 400, PEG 4000, and ethyl cellulose (200 mesh), and more preferentially selected from hydroxypropylmethyl cellulose E15, PEG 4000, and ethyl cellulose. The amount of the coating materials is usually from 0.5 to 20 portions (w/w).

In an preferred pharmaceutical product or dietary supplement, the amount by weight are APIs from 1 to 25 portions (w/w), surfactants from 5 to 200 portions (w/w), oil components from 0.5 to 100 portions (w/w), antioxidants from 1 to 20 portions (w/w), and other excipients from 0.5 to 1500 portions (w/w).

The compositions of the pharmaceutical products and dietary supplements described in this invention can be manufactured, at least, into tablet, capsule, pill, powder for injection, injection, lyophilized powder, ointment, suppository, cream, film, emulsion, spray or implant.

The formulations of the pharmaceutical products and dietary supplements described in this invention can be administered orally, intravenously, muscularly, subcutaneously, intracavitaryly, sublingually, anally, or topically.

The formulations of the pharmaceutical products and dietary supplements described in this invention can be used to treat and/or prevent prostatic diseases and skin cancer. The described prostatic diseases are preferentially referred to benign prostatic hyperplasia and prostatitis, particularly the benign prostatic hyperplasia.

Among the composition of the pharmaceutical products and dietary supplements described in this invention, the preferred ones have advantages of high dissolution rate, better stability, low doses, and fewer side effects.

Among the composition of the pharmaceutical products and dietary supplements described in this invention, the preferred ones contain phenethyl isothiocyanate (PEITC) as the active pharmaceutical ingredient (API), which can effectively inhibit and reduce the abnormal hyperplasia of the prostate tissue.

Among the composition of the pharmaceutical products and dietary supplements described in this invention, the preferred ones contain phenethyl isothiocyanate (PEITC) as the active pharmaceutical ingredient (API), which can effectively prevent and/or treat the inflammation of the prostate tissue.

Among the composition of the pharmaceutical products and dietary supplements described in this invention, the preferred ones contain phenethyl isothiocyanate (PEITC) as the active pharmaceutical ingredient (API), which can effectively inhibit the proliferation of skin cancer cells.

The dosage ranges of the composition containing one or more than one of isothiocyanates described in this invention for the treatment of benign prostatic hyperplasia and prostatitis are between 0.1 and 20 mg/kg, preferentially between 1 and 4 mg/kg. We demonstrated in this invention that among three different doses, i.e. 1, 2, and 4 mg/kg used in our experiments, the lowest dose of 1 mg/kg has already shown therapeutic activities against benign prostatic hyperplasia and prostatitis.

The composition of the pharmaceutical products and dietary supplements described in this invention, particularly those containing phenethyl isothiocyanate (PEITC) as API, can be used for the treatment of the diseases alone, or in combination with other therapies, such as surgery, one or more than one of the Western medicine or the Traditional Chinese Medicine, radiation, gene therapy and biologics etc.

In comparison with existing technology, the advantages of this invention are:

This invention demonstrates, for the first time, that isothiocyanates, including PEITC etc., effectively treat and/or prevent benign prostatic hyperplasia and prostatitis.

This invention further demonstrates that other isothiocyanates are similar to PEITC and are able to induce expression of phase II detoxification enzyme, i.e. glutathione S-transferase gene. All of those isothiocyanates are capable of increasing the ability of the prostatic cells to eliminate the toxic materials, thereby effectively treating and/or preventing prostate diseases and inflammations of other tissues/organs.

This invention demonstrates in a castrated rat model, for the first time, that isothiocyanates as exampled by PEITC are effectively against BPH.

This invention demonstrates in a rat model, for the first time, that isothiocyanates as exampled by PEITC can effectively treat and prevent prostatitis, particularly non-bacterial prostatitis.

This invention demonstrates for the first time that isothiocyanates significantly repress expressions of the androgen receptor (AR), Sp1, a upstream of AR gene, and prostate specific antigen (PSA), a downstream of AR gene in human prostate cancer cells.

This invention demonstrates for the first time that isothiocyanates as exampled by PEITC effectively inhibit the growth of B16 melanoma cells (skin cancer cell line).

This invention further provides, for the first time, formulations containing API of one or more of natural or synthetic isothiocyanates including PEITC etc.

This invention demonstrates that composition containing API of the isothiocyanates as exampled by PEITC is effective against BPH and prostatitis at low doses.

This invention demonstrates that composition of the pharmaceutical products and dietary supplements containing API of the isothiocyanates including PEITC etc. for the treatment of BPH and prostatitis has better dissolution rates, proved efficacy, minor side effects. They are effective at low doses, and are stable.

This invention provides a method of treating diseases of prostate. The described diseases of the prostate include, but not limited to BPH and prostatitis. The amount or dose of isothiocyanates or their derivatives or their metabolites in these applications is between 0.1 mg/kg and 20 mg/kg.

In one of particular example described in this invention, the dose of API at 1 mg/kg achieved good inhibitory therapeutic effect on BPH and prostatitis.

This invention further provides a method to repress expression of Phase II detoxification enzyme gene. The method includes following procedure: to expose prostate cells to one or more of isothiocyanates or their derivatives or their metabolites for certain period of time, and induce expression of the GSTP1 gene.

This invention also provides a method to treat skin cancer by using one or more of isothiocyanates or their derivatives or their metabolites to whom needed.

BRIEF DESCRIPTION OF FIGURES

FIG. 5, A typical histological slide section of normal prostate tissues (amplified by 20 times).

FIG. 6.1, A typical slide section of increasing density of prostatic acinars of benign prostatic hyperplasia (BPH) tissues of negative control (amplified by 20 times). This slide showed that the density of prostatic acinars was significantly increased as compared with normal prostatic gland.

FIG. 6.2, A typical slide section of enlarging lumen of prostatic acinars of benign prostatic hyperplasia (BPH) tissues of negative control (amplified by 20 times). The slide showed that the lumen of prostatic gland and secretary materials in the lumen of BPH were significantly increased as compared with normal prostatic gland.

FIG. 6.3, Effects of Proscar on the lumen of prostatic gland. This is a typical slide of benign prostatic hyperplasia from animal treated with positive control drug, Proscar (amplified by 20 times). The slide showed that the lumen of prostatic gland and secretary materials in the lumen of BPH were increased as compared with normal prostatic gland. At the same time the slide also showed that they were reduced as compared with untreated benign prostatic hyperplasia tissues of negative control.

FIG. 6.4, Effects of Proscar on the density of prostatic acinars. This is a typical slide of benign prostatic hyperplasia from animal treated with positive control drug, Proscar (amplified by 20 times). This slide showed that density of prostatic acinars was increased as compared with normal prostatic gland, but the density was reduced as compared with untreated BPH tissues of negative control.

FIG. 6.5, Effects of PEITC (2 mg/kg) on BPH (amplified by 20 times). This slide showed that the lumen, secretary materials in the lumen, and the density of prostatic acinars in BPH animals treated with 2 mg/kg PEITC were increased as compared with normal prostatic gland. But they were reduced as compared with untreated BPH tissues of negative control.

FIG. 7.1, Histological section of the prostatitis from an untreated prostatitis animal of negative control (amplified by 20 times). This slide showed congestion, edema, leukocyte infiltration and bleeding in the inflammatory prostatic gland.

FIG. 7.2, Histological section of the lymphocyte infiltration from an animal treated with Genurin (amplified by 20 times). This slide showed lymphocyte infiltration, fibrosis, and congestion.

FIG. 7.3, Histological section of the prostatitis from an animal treated with PEITC at dose of 4 mg/kg (amplified by 20 times). The slide showed that the prostatic tissues have edema, slight congestion and fibroid infiltration, but the histopathological scores were less severe than that of prostatic tissues from untreated prostatitis animals of negative control.

FIG. 7.4, Histological section of the prostatitis from an animal treated with PEITC at dose of 2 mg/kg (amplified by 20 times). The slide showed that the prostatic tissues have congestion, edema and fibroid infiltration.

FIG. 7.5, Histological section of the prostatitis from an animal treated with PEITC at dose of 1 mg/kg (amplified by 20 times). The slide showed that the prostatic tissues have congestion, edema and fibroid infiltration, leukocyte infiltration but they were less severe than that of prostatic tissues from untreated prostatitis animals of negative control.

EXAMPLES

Example 1

Preparation of Phenethyl Isothiocyanate (PEITC)

Figure 1:
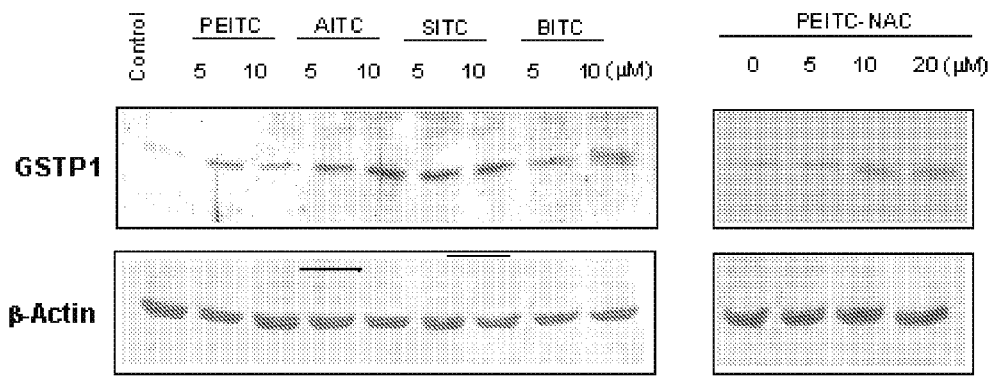
FIG. 1, Induction of phase II detoxification enzyme GSTP1 by various isothiocyanates in the human prostate cancer cell line LNCaP. PEITC: phenethyl isothiocyanate, BITC: benzyl isothiocyanate: AITC: allylisothiocyanate, SPITC: 4-sulfophenylisothiocyanate, and PEITC-NAC: N-acetylcysteine conjugate of phenethylisothiocyanate.

Instrument and Reagents:

$^1$H-NMR: Brucker AV-300, TMS was used as an internal standard, and $CDCl_3$ as solvent otherwise as indicated; Mass Spectrometer (MS): Nicolet FTMS-2000; Element analyzer: Elementar Vario EL III.

Thin layer Chromatography (TLC): Silicon $GF_{254}$ (Qingdao Ocean Chemical Plant, Qingdao, China) was used to prepare TLC plates. All reagents with either chemical grade or analytical grade were directly used without further treatment.

Example 1.1

Extraction of Phenethyl Isothiocyanate (PEITC) from Natural Plants a) Watercress was chopped and dipped in water for a few days under room temperature. The phenethyl isothiocyanate (PEITC) was produced by endogenous enzyme of the watercress during this procedure, and was extracted with water insoluble solvent such as N-hexane. The solvent was then removed by vacuum and the PEITC obtained with relative high yield and purity.

b) Phenethyl isothiocyanate (PEITC) could be also prepared from garden cress using the same method as above. After dipping the root of *Grass Oleaceae* in water, use water vapore distillation to obtain phenethyl isothiocyanate.

Example 1-2

Synthetic Preparation of Phenethyl Isothiocyanate (PEITC)

Fifteen ml of $CH_2Cl_2$ and 3 ml (40 mmol) of thiosulfate phosgene were added into a 50 ml round bottomed-flask, stirred and cooled to 0° C. Equivalent amount of triethylamine (4.04 g, 40 mmol) was then slowly added using a constant pressure drop liquid funnel (heat would be released, and the temperature should be controlled no higher than 15° C.). When it was finished, the reaction mixture was allowed to react for additional 5-6 hrs at room temperature. After the reaction was completed (no triethylamine was present in the reaction mixture as monitored by TLC), 10 ml of $H_2O$ was added to terminate the reaction. Additional 5 ml of $CH_2Cl_2$ was then added, and the organic phase was separated by a funnel, washed twice with water (15 ml×2), dried with anhydrous sodium sulfate, filtered, and condensed to dry. The residue was purified and eluted using petroleum ether (boiling point was between 60 and 90° C.) in a silicon column. After condensation and vacuum distillation, 4.9 g colorless and oily liquid of PEITC was obtained. The yield was approximately 75% and its chemical structure was confirmed by using NMR and MS as described by Katritzky and Victor Gil., et al (Alan R. Katritzky et al. 1979; Victor Gil et al, 1980).

Data of Structure Characterization:

$^1$H-NMR δ: 7.26-7.24 (m, 3H, Ph-H), 7.12 (d, J=8.5 Hz, 2H, Ph-H), 3.94 (t, J=7.0 Hz, 2H, $CH_2$), 2.81 (t, J=7.0 Hz, 2H, $CH_2$); ESI-MS: 164.1[M+H]$^+$, $C_9H_9NS$ (163.24); Anal. Calcd for $C_9H_9NS$:C66.22, H5.56, N8.58. Found: C66.30, H5.42, N8.34; Molecular weight: 163.24.

Example 2

Effects of Various Isothiocyanate on Expression of GSTP1 Protein

Materials and Methods:

Reagents:

PEITC was synthesized by Wuxi JC Pharmaceutical Technology Co., Ltd. and its chemical structure was confirmed by NMR, UV, IR and MS and the content and purity was analyzed by HPLC (>99%). Other isothiocyanates, benzyl isothiocyanate (BITC), allyl isothiocyanate (AITC), and 4-sulfophenylisothiocyanate (SPITC) were purchased from Sigma-Aldrich company (USA). N-acetylcysteine conjugate of phenethyl isothiocyanate (PEITC-NAC) was purchased from LKT Company (USA). The other chemicals were purchased from Sigma (St. Louis, Mo.) otherwise as indicated. Reagents for protein electrophoresis and nitrocelluse membrane were purchased from Bio-Rad Company (USA). The ELC Western detection kit and films were purchased from GE (USA). Antibodies against phase II detoxification enzyme GSTPI and β-actin, as well as the second antibody were purchased from BD and Santa Cruz Biotechnology, Inc. (USA), respectively.

Cell Culture:

The human prostate cancer cell lines LNCaP and PC-3 were purchased from the American Type Culture Collection (Rockville, Md.) and were maintained in RPMI-1640 (GIBCO, Gaithersburg, Md.) with 10% fetal bovine serum (FBS), penicillin—streptomycin and incubated at 5% $CO_2$ and 37° C.

Western blot to detect GSTP1 protein (FIG. 1): LNCaP cells at exponential growth phase were exposed to indicated concentrations of PEITC, BITC, AITC, SPITC, and PEITC-NAC for 24 hrs. The cells were harvested, washed and total cellular proteins were extracted as described previously (Wang, L. G., L. Ossowski, et al. Overexpressed androgen receptor linked to p21WAF1 silencing may be responsible for androgen independence and resistance to apoptosis of a prostate cancer cell line. Cancer Res 61(20): 7544-51, 2001). Fifty µg cellular extracts were separated on a SDS-PAGE, electro-transferred to nitrocellulose filters, and immunoblotted initially with antibodies against GSTP1. The same membranes were stripped and re-probed with β-actin for loading control. The result was recorded by ECL films.

Results and Discussion:

Using Western blot, we explored possible mechanisms by which isothiocyanates are effective against benign prostatic hyperplasia and prostatitis. As shown in FIG. 1, all isothiocyanates tested in this example under the same experimental conditions showed significant induction of GSTP1 expression. As a phase II detoxification enzyme, GSTP1 is able to effective neutralize endogenous and exogenous harmful agents including inflammatory components and carcinogens. It has been demonstrated that the GSTP1 gene was gradually shut off during the development of prostate diseases including prostatitis, benign prostatic hyperplasia and prostate cancer due to hypermethylation of CpG island in the promoter region of the GSTP1 gene. In this example, we clearly showed that PEITC and all other tested isothiocyanates which have isothiocyano-function group, significantly restored GSTP1 gene expression (FIG. 1). Thus, restoration of GSTP1 expression may be a major mechanism by which tested isothiocyanates effectively treat and prevent benign prostatic hyperplasia and prostatitis due to their isothiocyano-function group. Our study also demonstrates that isothiocyanates with isothiocyano-function group include 4-sulfophenylisothiocyanate (SPITC) and the metabolite (PEITC-NAC) of PEITC are effective agents for the prevention and treatment of prostate diseases.

Example 3

Inhibitory Effects of PEITC on Sp1 Transcription Factor

Materials and Methods

Reagents:

PEITC synthesized as Example 1-2 was dissolved in DMSO. The Sp1-luc and mtSp1-luc contain three tandem repeats of consensus Sp1 sites driving the luciferase gene and its mutant. They were used to evaluate the effects of PEITC on Sp1 expression. Effectene transfection reagent and luciferase assay kit were acquired from Qiagen (Valencia, Calif., USA) and Promega (Madison, Wis., USA). Reagents for protein electrophoresis were purchased from Bio-Rad company (USA). The other chemicals were purchased from Sigma (St. Louis, Mo.) otherwise as indicated.

Cell Culture:

The human prostate cancer cell line LNCaP AD was purchased from the American Type Culture Collection. LNCaP AI cell line was derived from LNCaP cells using a method described previously by Gao et al. (Gao, M., Ossowski, L., and Ferrari, A. C. Activation of Rb and decline in androgen receptor protein precede retinoic acid-induced apoptosis in androgen-dependent LNCaP cells and their androgen-independent derivative. J Cell Physiol, 179: 336-346, 1999). The AD and AI cells were maintained in RPMI-1640 with 10% fetal bovine serum (FBS) and charcoal stripped fetal bovine serum, penicillin-streptomycin for incubation at 5% $CO_2$ and 37° C. respectively.

Gene Transfection:

LNCaP AD or LNCaP AI cells grown exponentially were seeded into 60 mm dishes at a density of $10^5$ per ml. After incubation for 24 hrs at 5% $CO_2$ and 37° C., the cells were transfected with 1 µg/dish of SP1-luciferase gene (Sp1-luc), or its mutant mtSp1-luc using Effectene (Qiagen, Valencia, Calif.) as the transfection reagent. Twenty-four hrs after transfection, the cells were exposed for an additional 24 hrs to various concentrations of JC-5411(PEITC). The cells were collected, washed, lysed, and the lysates were used for luciferase activity assay using Promega luciferase assay system.

Mobility Gel Shift Assay (EMSA):

EMSA was performed according to modern technology. Briefly, AD cells grown exponentially were exposed to PEITC for 24 hrs. The extraction of nuclear proteins was performed as described previously (Wang, L. G., Liu, X. M., Kreis, W., and Budman, D. R. Down-regulation of prostate-specific antigen expression by finasteride through inhibition of complex formation between androgen receptor and steroid receptor-binding consensus in the promoter of the PSA gene in LNCaP cells. Cancer Res, 57: 714-719, 1997). Five µg of nuclear proteins was reacted for 30 minutes at room temperature with the [$^{32}$P]-labeled Sp1 oligonucleotide or their corresponding mutants oligonucleotide probe in binding buffer containing 1 g dIdC to increase the specificity of the reaction. The reaction mixtures were then subjected to electrophoresis in 8% native polyacrylamide gel(PAGE). The binding complexes were visualized by exposing the dried gel to X-ray film.

Figure 2:
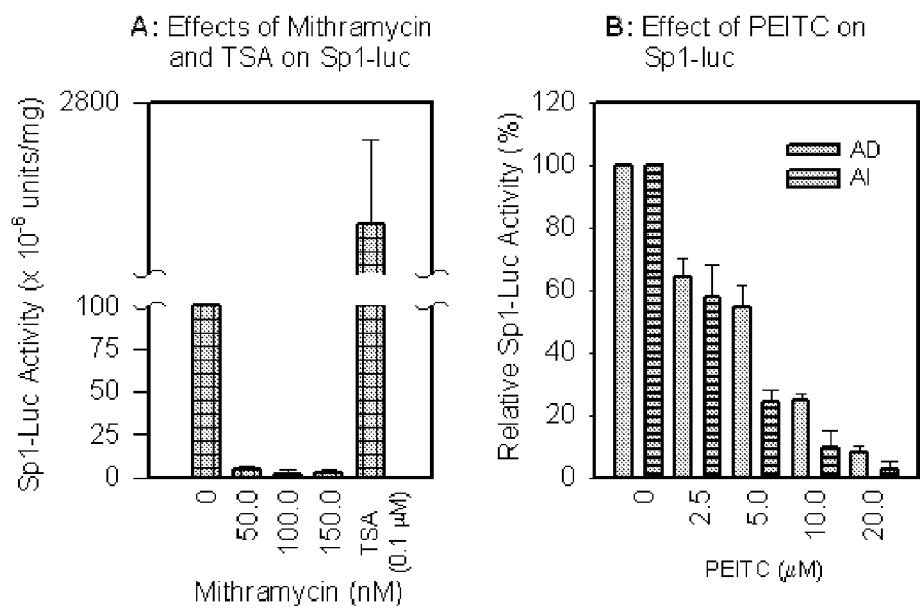
FIG. 2, Effect of phenethyl isothiocyanate (PEITC) on transcription factor, Sp1.

Results and Discussion:

In order to examine whether PEITC mediated inhibition of transcription factor SP1, the effects of PEITC on Sp1 specific luciferase transfection gene was investigated in which an Sp1 specific activation agent, trichostatin A (TSA) and Sp1 specific inhibitor, Mithramycin were used as controls to ensure the reliability of the test system. As shown in FIG. 2, treatment of SP1-luc transfected AD cells with PEITC for 24 hrs, the luciferase activity of transfected gene was significantly decreased which was similar to the positive control drug, Mithramycin. The inhibitory activity of PEITC on Sp1 expression was also found to be concentration dependent. In contrast, TSA significantly stimulated the luciferase activity. But no activity was observed when the mSp1-luc was used. This result demonstrated that PEITC is the transcription factor Sp1 inhibitor.

Figure 3:
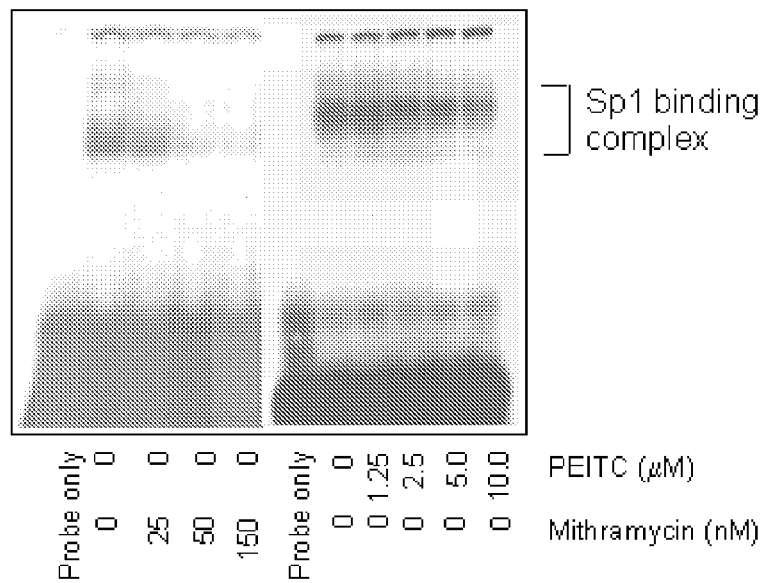
FIG. 3, Inhibition of phenethyl isothiocyanate (PEITC) on binding of Sp1 to the promoter DNA of androgen receptor.

To further explore possible mechanisms of PEITC inhibiting transcription factor Sp1, mobility gel shift assay (EMSA) was performed to examine effects of PEITC on Sp1-DNA binding. Sp1 is a transcription factor and its regulatory activity is through its binding to the SP1 binding site of the target gene promotor. EMSA is a common method to study the role, As shown in FIG. 3, after the treatment with PEITC, the binding activity to Sp1 specific oligonucleotide of nuclear proteins was significantly reduced in a concentration-dependent manner. This result not only indicates that PEITC is an Sp1 inhibitor, but also suggests that effect of PEITC on Sp1 downstream targets, such as SP1 specific luciferase transfection gene, is through its decreased Sp1-DNA binding complex formation.

Example 4

Effects of Various Isothiocyanates on AR, Sp1 and PSA Proteins

Materials and Methods:

Reagents:

Isothiocyanates were the same as Example 2. Other chemicals were purchased from Sigma (St. Louis, Mo.) otherwise as indicated. Reagents for protein electrophoresis and nitrocelluse membrane were purchased from Bio-Rad company (USA). The ELC Western detection kit and films were purchased from GE (USA). Antibodies against the AR, Sp1, PSA and β-actin etc. were purchased from BD Biosciences (USA) and Santa Cruz Biotechnology, Inc. (USA).

Figure 4:
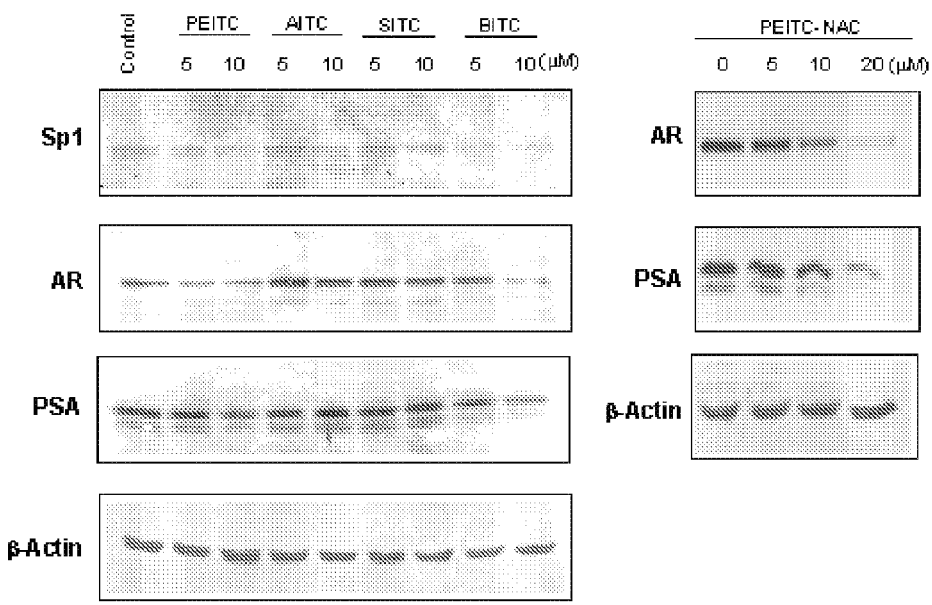
FIG. 4, Inhibitory effects of various isothiocyanates on the expressions of AR, AR upstream gene, Sp1, and AR downstream gene, prostate specific antigen (PSA) of the human prostate cancer cell line LNCaP. PEITC: phenethyl isothiocyanate, BITC: benzyl isothiocyanate, AITC: allyl isothiocyanate, SPITC: 4-sulfophenylisothiocyanate, and PEITC-NAC: N-acetylcysteine conjugate of phenethyl isothiocyanate.

Cell Culture:
The same procedures were used as described in Example 2.
Western blot to detect AR, SP1, PSA:
The human prostate cancer cell line LNCaP at exponential growth phase were exposed to PEITC, BITC, AITC, SPITC and PEITC-NAC for 24 hrs (shown in FIG. 4). The cells were harvested, washed and total cellular proteins were extracted as described previously (as Example 2). Fifty µg proteins were then subjected to electrophoresis in SDS-PAGE, electro-transferred to nitrocellulose filters, and immunoblotted initially with antibodies against AR, Sp1, and PSA. The same membranes were stripped and re-probed with β-actin for loading control. The result was recorded by ECL films.

Results and Discussion:
To further elucidate the effect of PEITC on SP1, other possible molecular mechanisms of isothiocyanates against growth of benign prostatic hyperplasia, prostatitis, prostate cancer was investigated by Western blot. The results showed that some isothiocyanates, particularly PEITC and BITC significantly inhibited expression of the AR, upstream gene of AR:Sp1 and downstream gene of AR:PSA (Shown in FIG. 4). While PEITC-NAC showed similar effects on those gene expressions, AITC only showed minimal activities, and no effect was achieved when the cells were treated with SPITC under the same experimental conditions. The results were in accordance with the inhibitory effect of these isothiocyanates on LNCaP cancer cells (Example 8). It is indicated that the inhibitory activity of these compounds on AR expression may be a molecular mechanism involved in selectively inhibiting proliferation of BPH and prostate cancer.

Based on the molecular mechanism study of the inhibitory effect of the isothiocyanates on BPH, prostatitis and prostate cancer, the in vitro and in vivo pharmacodynamics of the isothiocyanates were further studied.

Example 5

Therapeutic Effects of PEITC on BPH: Test One

Materials and Methods
Reagents:
PEITC was the same as Example 2. Testosterone propionate, estradiol, ketamine, and penicillin were purchased from Wuxi Shanhe Health Drug Chain Limited Participation Group.

Animals:
Adult pathogen-free SD rats, male, body weight ranging from 150 to 200 grams, were purchased from the Animal Center of Nanjing Medical University. The animals were housed five per cage and fed ad libitum, fresh tap water and commercial rodent pellets. Animal rooms were controlled at 25±2° C. and a 12 hrs light/dark cycle.

Disease Model and Drug Treatment:
Sixty male SD rats were randomly divided into 6 groups, ten each. The animals were anesthetized using ketamine and castrated by removing testis under sterile conditions. After the surgery, the penicillin was injected to prevent the animals from infection. One week later, the testosterone propionate was injected subcutaneously at dose of 1 mg/rat for a month, once a day. Group 1 was served as a negative control group, and the animals of group 1 were given saline orally without any active pharmaceutical ingredient for a month beginning on the same day the testosterone propionate was injected. Group 2 was served as positive control group in which animals were given estradiol subcutaneously at a dose of 0.1 mg/rat for a month beginning on the same day the testosterone propionate was injected. Groups from 3 to 6 was served as drug treatment groups in which animals were given tested articles on the same day the testosterone propionate was injected. The animals in groups from 3 to 6 were given PEITC composition (oil base and aqueous base) for a month, once a day, by gavage at doses of 4 mg/kg (API of the Formulation of Example 13-3), 1 mg/kg (API of the Formulation of Example 13-3), 4 mg/kg (API of the Formulation of Example 13-11) and 1 mg/kg (API of the Formulation of Example 13-11), respectively.

Twenty-four hrs after the last dosage, the animals were euthanized and weighed. Volume and weight of prostate were measured. The averages of volume/weight and organ coefficient (average weight of prostate/average of body weight) were calculated, and statistical analysis performed (t test).

Results and Discussion:
While the average weight of prostate in animals from negative control group was found to be 1.28 grams, and its organ coefficient was 0.34%, the average tissue weight and organ coefficient in animals from positive control group, however, was found to be 0.73 grams and 0.23%, respectively. The average weight of prostate in animals from groups treated with PEITC was found to be 0.79 g (oil base formulation at dose of 4 mg/kg), 0.91 g (oil base formulation at dose of 1 mg/kg), 0.83 g (aqueous base formulation at dose of 4 mg/kg) and 0.75 g (aqueous base formulation at dose of 1 mg/kg), and their organ coefficient was 0.23%, 0.25%, 0.23%, and 0.21%, respectively. They were significantly lower than the negative control group (P<0.05), demonstrating that the hormone effectively induced BPH and isothiocyanates, as exampled by PEITC in either oil or aqueous preparation was able to inhibit the BPH, and the activity was equal to the positive control drug, estradiol. This example indicated that PEITC was effective to inhibit BPH at the experimental dose range.

Example 6

Therapeutic Effects of PEITC on BPH: Test Two

Materials and Methods
Reagents:
PETIC was the same as Example 2. Testosterone propionate, Proscar, ketamine, and penicillin were purchased from Wuxi Shanhe Health Drug Chain Limited Participation Group.

Animals:
Adult pathogen-free SD rats, male, body weight ranging from 150 to 200 grams, were purchased from the Animal Center of Nanjing Medical University. The animals were housed five per cage and fed ad libitum, fresh tap water and commercial rodent pellets. Animal rooms were controlled at 25±2° C. and a 12 hrs light/dark cycle.

Disease Model and Drug Treatment:
Thirty-six male SD rats were randomly divided into 4 groups, nine each. Group 1 was served as blank control group (pseudo-surgery control group) in which animals were under the same surgical procedures except no testis was sectioned and fed normally. Groups from 2 to 4 were served as treatment groups in which all animals were anesthetized using ketamine and castrated by removing both testises under sterile conditions. After the surgery, the penicillin was injected to prevent the animals from infection. One week later, the testosterone propionate was injected subcutaneously at dose of 5 mg/kg, once a day for a month. Group 2 was served as negative control in which animals were given saline orally for a month on the same day that the testosterone propionate was injected, once a day. Group 3 was served as positive control group in which animals were given Proscar by gavage at dose of 0.1 mg/rat/day for a month beginning on the same day that the testosterone propionate was injected. Animals in the group 4 were orally treated with aqueous base formulation of PEITC (Example 13-11) at dose of 2 mg/kg, once a day, for a month beginning on the same day that the testosterone propionate was injected.

Twenty-four hrs after the last dose, the animals were euthanized and weighed. Volume and weight of prostate were measured. The averages of prostate volume/weight and organ coefficient (average weight of prostate/average of body weight) were calculated, and statistical analysis performed (t test).

Histopathology:

Prostate tissues of animals from different groups were embedded with paraffin. The tissue sections were stained with H&E for histpathological examination by an anatomical pathologist.

The experimental data were shown in Table 1&2.

showed that both Proscar and PEITC were effective. From the comparison of the efficacy data between Proscar and PEITC, we found that PEITC might have better therapeutic activity than Proscar, which needs to be further confirmed by more experiments.

The histopathological examinations showed that major histopathological changes in the BPH of the tested rats include abnormal acinar density, enlargement of lumen of gland, abnormal secretions of gland, together with connective tissue proliferation and papillary hyperplasia. As shown in Table 2, FIG. 5, FIG. 6.1-6.5, the pathological changes of the animals treated with PEITC and Proscar were significantly less severe than the negative control group (Proscar, $P<0.05$; PEITC $P<0.01$). They were similar to the data of the weights and volumes of the prostate, as well as the organ coefficients indicated that the pathological changes of the animals treated with PEITC was not so obvious compared with Proscar control group.

TABLE 1

Inhibitory effects of PEITC on androgen-induced BPH in rats

|  | Average Body Weight (g) | Average Weight of Prostate (g) | Average Volume of Prostate (cm$^3$) | Organ Coefficient (%) | Inhibition of Organ Coefficient (%) |
|---|---|---|---|---|---|
| Blank Control | 415 ± 14.1 | 0.78 ± 0.07 | 0.87 ± 0.12 | 0.187 ± 0.01 |  |
| Negative Control | 330 ± 22.6 | 1.41 ± 0.14 | 1.68 ± 0.17 | 0.43 ± 0.004 |  |
| Positive Control (Proscar, 0.5 mg/kg) | 340 ± 30.5 | 1.30 ± 0.12 | 1.61 ± 0.16 | 0.38 ± 0.05 | 11.63 |
| PEITC (2 mg/kg) | 337 ± 23.7 | 1.20 ± 0.16 | 1.42 ± 0.16 | 0.36 ± 0.06 | 16.28 |

TABLE 2

Hispathological scores of BPH in animals from different groups.

| Group | No. of Animals | Acinar Density (Scores/No.) | | | | Enlargement of Lumen of Gland (Scores/No.) | | | | Secretions of Gland (Scores/No.) | | | | Connective tissue proliferation, or papillary hyperplasia (Scores/No.) | | | | Average X ± SD |
|---|---|---|---|---|---|---|---|---|---|---|---|---|---|---|---|---|---|---|
| Scores$^a$ |  | 0 | + | ++ | +++ | 0 | + | ++ | +++ | 0 | + | ++ | +++ | 0 | + | ++ | +++ |  |
| Negative Control | 9 | 1 | 2 | 6 | 0 | 1 | 3 | 5 | 0 | 2 | 2 | 5 | 0 | 6 | 2 | 1 | 0 | 4.78 ± 1.64 |
| Positive Control (Proscar) | 9 | 1 | 2 | 6 | 0 | 3 | 3 | 3 | 0 | 5 | 2 | 2 | 0 | 8 | 1 | 0 | 0 | 3.33 ± 1.11* |
| PEITC | 9 | 7 | 2 | 0 | 0 | 3 | 6 | 0 | 0 | 3 | 5 | 1 | 0 | 8 | 1 | 0 | 0 | 1.78 ± 1.09** |

$^a$0, +, ++, and +++ represent score 0, 1, 2, and 3 respectively.
*P < 0.05 as compared with negative control;
**P < 0.01 as compared with negative control Results and Discussion:

Based on the comparison of the data of the blank control group and those of the negative control group, the rats of the negative control group had obvious prostate hyperplasia, indicating that BPH rat model was valid as shown in Table 1. Also shown in Table 1, treatment of Proscar and PEITC can reduce the volume of the prostate. Since BPH is a chronic disease, we speculated that a better efficacy could be achievable if the BPH animals are treated with either Proscar or PEITC for longer period of time, not just one month. The data of the weight and volume of prostate, organ coefficient Example 7

Therapeutic Effects of PEITC on Non-Bacterial Prostatitis

Materials and Methods

Reagents:

PEITC was the same as Example 2. Xiaozhiling injection (Tannin potassium aluminum sulfate injection) was purchased from Jinan Yongning Pharmaceutical Co., Ltd.

GENURIN (Flavoxate Hydrochloride), ketamine, and penicillin were purchased from Wuxi Shanhe Health Drug Chain Limited Participation Group.

Animals:

Adult pathogen-free SD rats, male, body weight ranging from 150 to 200 grams, were purchased from the Animal Center of Nanjing Medical University. The animals were housed five per cage and fed, ad libitum, fresh tap water and commercial rodent pellets. Animal rooms were controlled at 25±2° C. and a 12 hrs light/dark cycle.

Disease Model and Treatment:

Fifty-five male SD rats were randomly divided into 6 groups, 9 each, except the negative control group for which 10 animals were used. All animals from group 1 to 6 were anesthetized by injection of ketamine under sterile conditions and incised around 1.5 cm with a sterilized surgery scalpel at middle of abdomen. Animals in Group 1 were injected penicillin to prevent infection, and given distill water, 10 ml/kg, once a day, 5 times a week for 5 weeks. Groups from 2 to 6 injected 25% Xiaozhiling into left and right lobes of prostate, 0.1 ml for each lobe and sew the muscle and skin with #1 silk thread. The animals were then given penicillin to prevent infectious. Group 2 was served as negative control group in which animals were treated with distill water by gavage 24 hrs after the Xiaozhiling injection, once a day, 5 times a week for 5 weeks. Group 3 was served as positive control group in which animals were treated with GENURIN by gavage 24 hrs after the Xiaozhiling injection at dose of 60 mg/kg, once a day, 5 times a week (escaping weekend) for 5 weeks. Groups 4 to 6 were treated by gavage with 4, 2, and 1 mg/kg of PEITC formulation described in Example 13-11 for the same period of time as positive control group (once a day, 5 times a week for 5 weeks). On the last dosing day, urine samples from different groups that covered periods of 1, 2 and 3 hrs were collected.

Twenty-four hrs after the last dose, the animals were euthanized and weighed. Volume and weight of prostate were measured. The averages of the prostate weight/volume and organ coefficient (average weight of prostate/average of body weight) were calculated, and statistical analysis performed (t test).

Histopathology:

Prostate tissues of animals from different groups were embedded with paraffin. The tissue sections were stained with H&E for histpathological examination by an anatomical pathologist.

Results and Discussion

The results were summarized in Table 3 below.

TABLE 3

Inhibitory effect of PEITC on enlarged prostate.

| | Average of Body Weight (g) | Average Weight of Prostate(g) | Average Volume of Prostate (cm$^3$) | Organ Coefficient(%) | Inhibition of Organ-coefficient (%) |
|---|---|---|---|---|---|
| Blank Control | 417 ± 13.8 | 0.77 ± 0.05 | 0.85 ± 0.14 | 0.185 ± 0.02 | |
| Negative Control | 399 ± 14.4 | 1.03 ± 0.14 | 1.10 ± 0.20 | 0.260 ± 0.04 | |
| Positive Control (GENURIN 60 mg/kg) | 356 ± 25.9 | 0.71 ± 0.09 | 0.69 ± 0.10 | 0.196 ± 0.03* | 24.62 |
| PEITC (1 mg/kg) | 377 ± 39.1 | 0.7 ± 0.15 | 0.78 ± 0.16 | 0.186 ± 0.03* | 28.46 |
| PEITC (2 mg/kg) | 360 ± 24.8 | 0.70 ± 0.12 | 0.82 ± 0.13 | 0.188 ± 0.03* | 27.69 |
| PEITC (4 mg/kg) | 370 ± 24.8 | 0.72 ± 0.16 | 0.78 ± 0.10 | 0.192 ± 0.03* | 26.15 |

*P < 0.05 as compared with negative control.

TABLE 4

Diuretic effect of PEITC on animals with prostatitis

| | 1 h Period (ml) | 2 h Period (ml) | 3 h Period (ml) |
|---|---|---|---|
| Blank Control | 3.5 ± 1.2 | 7.8 ± 1.7 | 8.1 ± 1.7 |
| Negative Control | 3.6 ± 1.6 | 8.0 ± 1.7 | 8.1 ± 1.9 |
| Positive Control (GENURIN 60 mg/kg) | 6.2 ± 1.3* | 7.9 ± 1.9 | 8.8 ± 1.2 |
| PEITC (1 mg/kg) | 5.5 ± 1.0* | 7.0 ± 0.7 | 7.9 ± 1.0 |
| PEITC (2 mg/kg) | 6.6 ± 2.1* | 8.7 ± 1.7 | 9.2 ± 2.7 |
| PEITC (4 mg/kg) | 5.7 ± 2.2* | 9.4 ± 1.5 | 10.4 ± 1.9* |

*P < 0.05 as compared with negative control

TABLE 5

Results of histophatological examination of SD rats prostatitis

| Group | No. of Animal | Congestion | | | | Edema | | | | Inflammatory Infiltration | | | | Chronic Inflammatory Infiltration | | | |
|---|---|---|---|---|---|---|---|---|---|---|---|---|---|---|---|---|---|
| Scores[a] | | 0 | + | ++ | +++ | 0 | + | ++ | +++ | 0 | + | ++ | +++ | 0 | + | ++ | +++ |
| Negative Control | 10 | 4 | 3 | 3 | 0 | 6 | 1 | 3 | 0 | 7 | 1 | 2 | 0 | 9 | 1 | 0 | 0 |
| GENURIN | 9 | 4 | 5 | 0 | 0 | 6 | 2 | 1 | 0 | 7 | 2 | 0 | 0 | 5 | 4 | 0 | 0 |

TABLE 5-continued

Results of histophatological examination of SD rats prostatitis

| | | | | | | | | | | | | | | | | | |
|---|---|---|---|---|---|---|---|---|---|---|---|---|---|---|---|---|---|
| PEITC (4 mg/kg) | 9 | 7 | 2 | 0 | 0 | 5 | 4 | 0 | 0 | 7 | 2 | 0 | 0 | 9 | 0 | 0 | 0 |
| PEITC (2 mg/kg) | 9 | 4 | 5 | 0 | 0 | 6 | 3 | 0 | 0 | 6 | 3 | 0 | 0 | 8 | 1 | 0 | |
| PEITC (1 mg/kg) | 9 | 3 | 6 | 0 | 0 | 3 | 6 | 0 | 0 | 9 | 0 | 0 | 0 | 9 | 0 | 0 | |

| Group | Bleeding | | | | Fibrous Exudation | | | | Hyperblastosis | | | | Overall Average X ± SD |
|---|---|---|---|---|---|---|---|---|---|---|---|---|---|
| Scores[a] | 0 | + | ++ | +++ | 0 | + | ++ | +++ | 0 | + | ++ | +++ | |
| Negative Control | 5 | 4 | 1 | 0 | 3 3 | 3 1 | | | 7 | 3 | 0 | 0 | 4.20 ± 1.87 |
| GENURIN | 6 | 3 | 0 | 0 | 8 0 | 1 0 | | | 8 | 1 | 0 | 0 | 1.83 ± 0.75** |
| PEITC (4 mg/kg) | 6 | 3 | 0 | 0 | 4 1 | 4 0 | | | 9 | 0 | 0 | 0 | 1.72 ± 0.79** |
| PEITC (2 mg/kg) | 8 | 1 | 0 | 0 | 5 0 | 4 0 | | | 7 | 2 | 0 | 0 | 2.16 ± 1.52** |
| PEITC (1 mg/kg) | 7 | 2 | 0 | 0 | 5 0 | 4 0 | | | 7 | 2 | 0 | 0 | 1.83 ± 1.06** |

[a] 0, +, ++, and +++ represent score 0, 1, 2, and 3 respectively
**$P < 0.01$ as compared with negative control.

As shown in Table 3, PEITC effectively inhibited the prostate enlargement caused by prostatitis. This effect however, did not closely relate to dosages indicating that the lowest dose may already reach the optimal activity. On the other hand, PEITC showed significant diuretic effect in a dose-dependent manner. The higher dose, the better diuretic effect was seen (Table 4). Diuretic effect of PEITC at dose of 4 mg/kg achieved statistically significance ($P<0.05$) as compared with untreated control, and this therapeutic effect was found to be better than that of positive control drug, GENURIN. Importantly, histopathological examinations showed that all histopathological grades from animals treated with either PEITC or the positive control drug, GENURIN were statistically lower than that of untreated control ($P<0.01$). These data further provided solid evidence that PEITC was equal to GENURIN in terms of reduction of symptoms and histopathological lesions of prostatitis (Table 5 and FIG. 5, 7.1-7.5).

Example 8

Effects of Isothiocyanates on Human Prostate Cancer Cells Growth In Vitro

Materials and Methods

Reagents:

Phenethyl isothiocyanate (PEITC) was the same as Example 2. Other isothiocyanates, i.e. benzyl isothiocyanate (BITC), allyl isothiocyanate (AITC), 4-sulfophenylisothiocyanate (SPITC), were purchased from Sigma-Aldrich (USA). The working solutions of the above isothiocyanates were prepared in DMSO except SPITC for which serum-free RPMI 1640 medium was used as a solvent.

Cell Culture:

The same procedures were used as described in Example 2.

Determination of Cell Growth:

MTT and SRB method as described in the reference (Kreis, Budman et al. 1997). Briefly, human prostate cancer cells grown exponentially were aliquoted into 96-well plates at a density of 5000 cells/200 μl per well. Twenty-four hrs after the incubation, the cells were exposed for three or seven days to serial dilutions of indicated isothiocyanate. After the incubation, 100 μl of the medium was removed from each of the wells and 50 μl solution of 3-(4,5-dimethyl-thiazol-2-yl)-2,5-diphenyltetrazolium bromide (MTT) was added, the cells were incubated for an additional 4 hrs and then 200 μl of 0.04 N HCl-isopropanol was added to each well to dissolve the black formazan precipitates. The absorbance was measured at wavelength 540 nm. For SRB method, remove the medium after 72 hrs. The cells on 96-well dishes were fixed with 10% trichloride acetic acid for 1 hr, air-dried for 24 hrs. The cells were then stained with 50 μl of SRB (sulforhodamine B) for 20-30 mM. After extensive washes with 1% acetic acid for 5 times, air-dried, the purple protein-SRB complex was dissolved in 200 μl 10 mM Tris-HCl buffer (pH 10.0), and the absorbance was measured at the wavelength of 540 and 630 nm. The percent of cell survival (T/C%) were calculated based on the results of test groups to that of the control group. All of the test data were summarized in the following Table 6. The semi-exponential curves of the percent of cell survival (T/C%) to the drug concentrations (FIG. 8) and $IC_{50}$ were obtained by using Sigma-plot program.

TABLE 6

Inhibitory effects of isothiocyanates on the growth of human prostate cancer cell line LNCaP

| Concentrations (μM) | Percent of Cell Survival (T/C %) | | | |
|---|---|---|---|---|
| | PEITC | BITC | SPITC | AITC |
| 0.0390 | 102.60 | 94.09 | 99.54 | 98.84 |
| 0.0780 | 102.10 | 95.64 | 101.43 | 98.92 |
| 0.1562 | 88.10 | 97.91 | 101.43 | 98.26 |
| 0.3125 | 82.25 | 95.82 | 99.66 | 98.55 |
| 0.6250 | 82.25 | 71.25 | 98.26 | 97.10 |
| 1.2500 | 78.12 | 27.95 | 101.56 | 99.49 |
| 2.5000 | 30.24 | 14.83 | 104.37 | 83.95 |
| 5.0000 | 10.06 | 5.07 | 100.60 | 47.60 |
| 10.0000 | 1.52 | 0.88 | 101.33 | 41.01 |
| 20.0000 | 0.56 | 0.94 | 99.88 | 38.69 |

Results and Discussion

Figure 8:
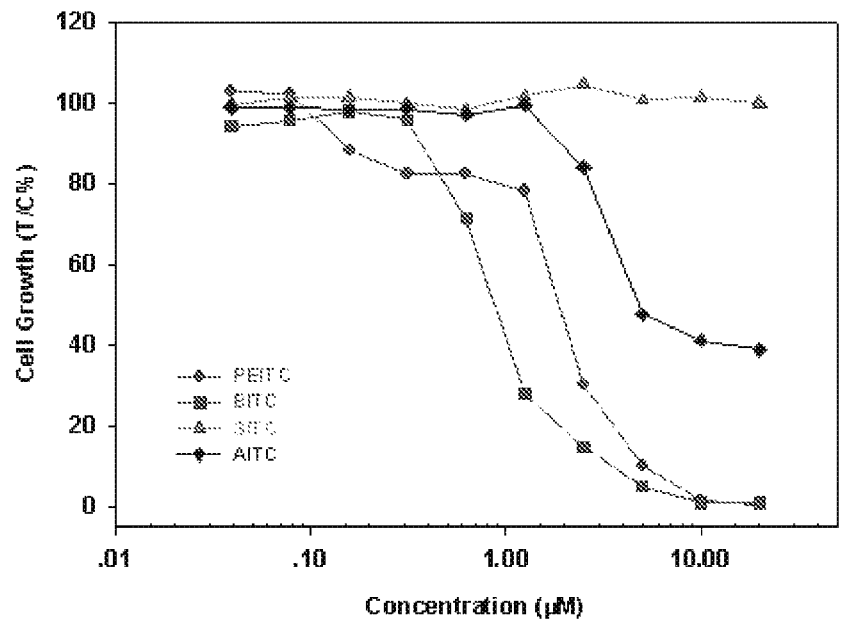
FIG. 8, Comparison of cell growth inhibition among different isothiocyanates in the human prostate cancer cell line LNCaP. PEITC: phenethyl isothiocyanate, BITC: benzyl isothiocyanate: AITC: allyl isothiocyanate, SPITC: 4-sulfophenylisothiocyanate.

Using both MTT and SRB, we examined the effects of various isothiocyanates (PEITC, BITC, AITC and SPITC) on human prostate cancer cell LNCaP growth and compared their activities. We found that all tested isothiocyanates except SPITC were able to significantly inhibited prostate cancer cell growth within the tested concentrations (0.039 to 20 μM). PEITC and BITC showed similar growth inhibitory activity with an $IC_{50}$ between 0.8 to 1.5 μM, but AITC was relatively weaker with an $IC_{50}$ approximately 10 μM (FIG. 8). These observations suggest that the growth inhibition on prostate cancer cells or on other malignant cells is one of common biological or pharmacological characteristics of isothiocyanates. We also observed as described in Example 11, that much higher concentration was needed for PEITC to achieve $IC_{50}$ on growth inhibition of B16 mouse melanoma cell line ($IC_{50}$ was approximately between 10-20 μM). The inhibitory effect on the growth of human prostate cancer cells was stronger (8-10 times) than B16 cells. These results suggest that human cancer cells are more sensitive to isothiocyanates than animal cancer cells or human prostate cancer cells are more sensitive than other cancer cells.

Example 9

Figure 9:
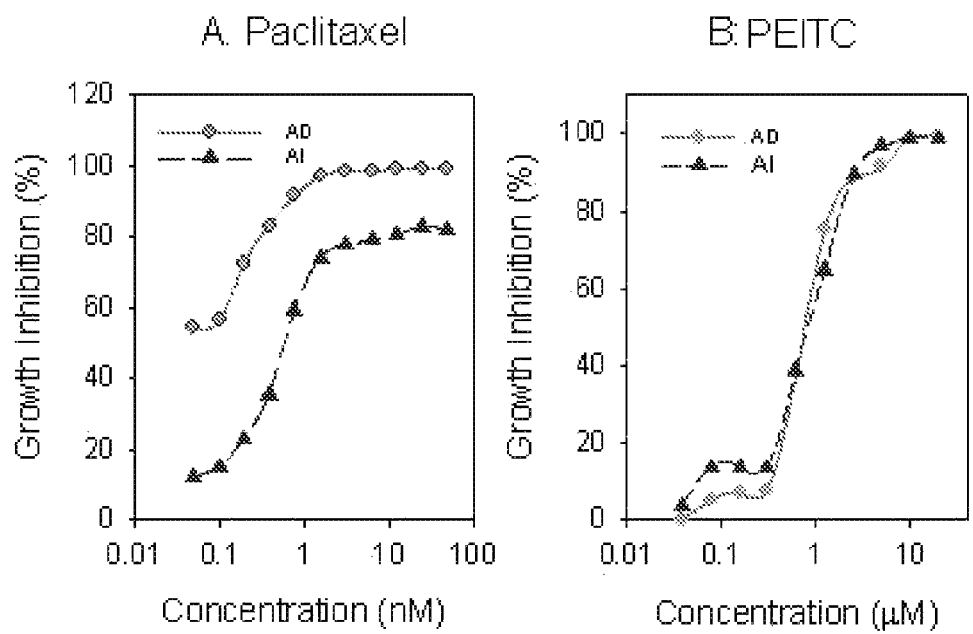
FIG. 9, Effects of phenethyl isothiocyanate (PEITC) on expression of endogenous androgen receptor (AR) and AR downstream gene-prostate specific antigen (PSA).

Growth Inhibitory Effects of PEITC on Hormone-Dependent and Independent Prostate Cancer Cells Materials and Methods
  Reagents:
  Phenethyl isothiocyanate (PEITC) was the same as Example 2. Other chemicals were purchased from Sigma-Aldrich (USA), otherwise as indicated.
  Cell Culture: Human Prostate Cancer Cell Line LNCaP.
  The same procedures were used as described in Example 3.
  MTT: MTT and SRB method were used to determine the effects of various isothiocyanates on cell growth as described previously (Kreis, Budman et al, 1997). Briefly, human prostate cancer cell line LNCaP grown exponentially were aliquoted into 96-well plates at a density of 2500 cells/200 μl per well. Twenty-four hrs after the incubation, the cells were exposed for seven days to serial dilutions of indicated isothiocyanate or paclitaxel. After the incubation, 100 μl of the medium was removed from each of the wells and 50 μl of a 1 mg/ml solution of 3-(4,5-dimethyl-thiazol-2-yl)-2,5-diphenyltetrazolium bromide (MTT) was added, the cells were incubated for an additional 4 hrs and then 200 μl of 0.04 N HCl-isopropanol was added to each well to dissolve the black formazan precipitates. The absorbance was measured at wavelength 540 nm. The percent of cell survival (T/C%) were calculated based on the results of test groups to that of the control group. The semi-exponential curves of the percent of cell survival (T/C%) to the drug concentrations and $IC_{50}$ were obtained by using Sigma-plot program.
Results and Discussion
  Since the overactivated androgen-androgen receptor (AR) is an important factor involved in the uncontrolled prostate and prostate cancer cell proliferation, and is as important as, might much important to hormone independent prostate cancer cell. thus, blockage of the translation and expression of AR is expected to suppresses growth of both hormone-dependent and independent prostate cancer cell. Therefore, in this experiment, we used MIT method to examine the inhibitory effects of PEITC on prostate cancer cell growth, and compared the activity between hormone dependent (LNCaP AD) and hormone independent (LNCaP AI) cell lines. As shown in FIG. 9B, a significant protate cancer cell growth inhibition of PEITC was observed. More importantly, an almost equal $IC_{50}$ (0.6 μM) was observed in both AD and AI cell lines. Under the same experimental conditions, paclitaxel, a clinical widely used anticancer drug also achieved significant growth inhibition. However, when we compared the $IC_{50}$ between AD and AI in response to paclitaxel, we found that, in contrast to PEITC, AI cells showed significant resistance to paclitaxel as indicated by 60 times higher of $IC_{50}$ ($IC_{50}$ was found to be 0.01 nM for AD and 0.6 nM for AI cells, FIG. 9A). The results were in accordance with those we observed before. The data also demonstrated that the activity of paclitaxel was much higher than that of PEITC, but given the fact that paclitaxel has high toxicities while it achieves therapeutic effects. For example, when paclitaxel plasma concentration is at 0.05 μM, it will produce severe bone marrow suppression. In contrast, PEITC is present in natural food, and has lower toxicities/side effects. The clinical data has demonstrated that paclitaxel could not prolong the life of the patients of the post stage of prostate cancer besides its toxicities.

Example 10

Anti Cancer Activities In Vivo and Effects on AR Expression of PEITC-NAC

Materials and Methods
  Reagents:
  PEITC-NAC was the same as Example 2. Other chemicals were purchased from Sigma-Aldrich (USA), otherwise as indicated.
  Xenograft Tumor and Treatment:
  Immunodeficient BALB/c nude mice, male, 5 weeks old, were purchased from Animal Center, Chinese Academy of Sciences, Shanghai, China. The animals were housed in an SPF animal lab. Human androgen independent prostate cancer PC-3 cells, in the form of a pellet (approximately 1×106 cells per animal), were mixed with a 50% volume of Matrigel and implanted s.c. in the flank of the animal. Twenty-four hrs after the transplant, the mice were randomly divided into two groups, eight animal each. One group served as untreated control and fed with regular AIN76 diet, and another one as treatment group in which AIN76 diet containing 8 μM/g of PEITC-NAC was provided. The animals were treated for 30 days, and tumor incidence and size were measured at day 7, 10, 22. Twenty-four hrs after the last administration, animals were euthanized, and body and tumors were weighted. The percentages of the turner inhibition were calculated and, the results were shown in Table 7. Western blot was used to follow the possible change of AR expression.

TABLE 7

Anticancer activities of PEITC-NAC on xenograft hormone independent human prostate cancer cell line PC-3

| | Untreated Control | | | PEITC-NAC at Different Days | | | |
| --- | --- | --- | --- | --- | --- | --- | --- |
| Days After Tumor Inplantation | No. of Animals with Tumor | No. of Animals without Tumor | Incidence (%) | No. of Animals with Tumor | No. of Animals without Tumor | Incidence (%) | Inhibition (%) |
| 7 | 7 | 1 | 87.5 | 6 | 2 | 75 | — |
| 10 | 8 | 0 | 100 | 6 | 2 | 75 | — |

TABLE 7-continued

Anticancer activities of PEITC-NAC on xenograft hormone independent human prostate cancer cell line PC-3

| | Untreated Control | | | PEITC-NAC at Different Days | | | |
|---|---|---|---|---|---|---|---|
| Days After Tumor Inplantation | No. of Animals with Tumor | No. of Animals without Tumor | Incidence (%) | No. of Animals with Tumor | No. of Animals without Tumor | Incidence (%) | Inhibition (%) |
| 22 | 8 | 0 | 100 | 7 | 1 | 87.5 | — |
| At Terminal | 8 | 0 | 100 | 7 | 1 | 87.5 | 53.3 |

Results and Discussion

Immunodeficient xenograft tumor models were widely used to evaluate therapeutic activities of new potential anticancer drugs. In order to examine the possible anticancer activity of PEITC-NAC, xenograft model of human androgen independent PC-3 prostate cancer cells was used. As shown in Table 7, PEITC-ANC effectively inhibited PC-3 tumor growth by 53.3% (P<0.02) at given dose. More interestingly, one animal was cancer-free.

Example 11

Growth Inhibitory Effects of PEITC on Mouse B16 Melanoma In Vitro

Materials and Methods

Reagents:

PEITC was the same as Example 2. Mouse B16 melanoma cell line was purchased from the Shanghai Institute of Cell Biology, Chinese Academy of Sciences, Shanghai, China. Fetal bovine serum (FBS) was purchased from Shanghai Hua-Mei Biochemical Reagents Company. RPMI 1640 medium was purchased from Gibco. Penicillin and streptomycin were medical products. Glutamine and trypan blue were provided by Sigma Company. Trypsin was from Amresco. 24-well cell culture plates were provided by Costar Company (US). Dimethyl sulfoxide (DMSO) was purchased from Shanghai Medical/Shanghai Chemical Reagents Company.

Cell Culture:

RPMI 1640 medium was adjusted to pH7.0~7.2 by using 1 mol/L HCl or NaOH, sterilizing filtration, then kept at 4° C. in a refrigerator. Before using, 10% FBS, 1% 200 mmol/L glutamine, 100 U/ml Penicillin and 100 U/ml streptomycin were added in to make a working medium. B16 mouse melanoma cells were cultured in the medium at 37° C. with saturated moistures in 5% $CO_2$ incubator.

Figure 10:
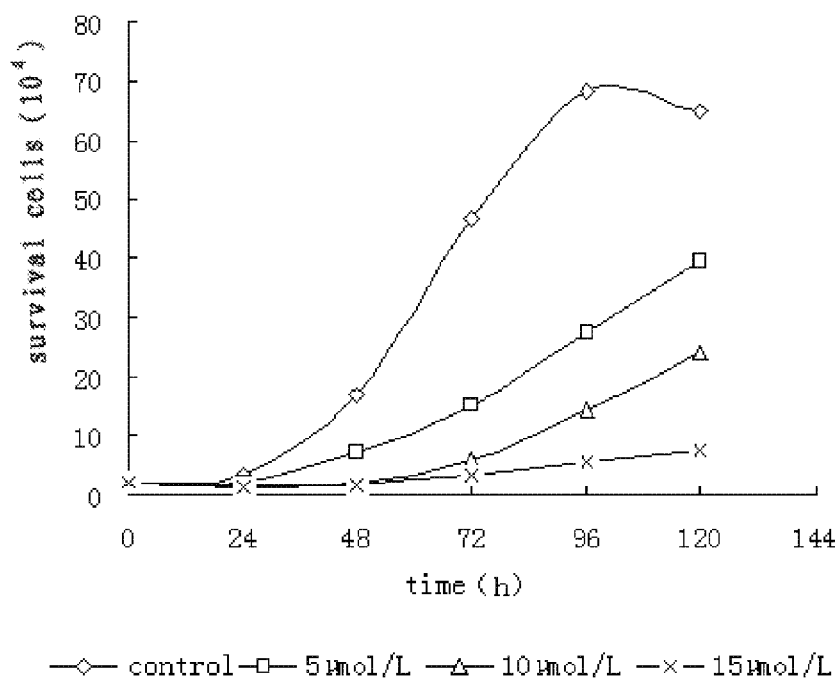
FIG. 10, Effects of phenethyl isothiocyanate (PEITC) on growth curve of B16 (mouse melanoma cell line)

Determination of Cell Growth Curve:

B16 mouse melanoma cells at exponential growth phase were digested by 0.25% trypsin, adjusted to the density of $2\sim5\times10^4$/mL by adding the above working RPMI 1640 medium, sed into 24-well dishes at 1 ml per well, under normal culture conditions mentioned above. Twenty-four hrs after the incubation, the cells were exposed to 5, 10, and 15 µM of PEITC in triplet, respectively. Equal volume of the working RPMI 1640 medium was added into the wells of the control group. The cell numbers from each well were counted in triple using trypan blue exclusion method from day 0 to day 5. The cell growth curve was obtained by plotting the mean of cell numbers at each time points with the time (FIG. 10).

Determination of Cell Growth Inhibition:

B16 mouse melanoma cells at exponential growth phase were digested by 0.25% trypsin, adjusted to the density of $3\sim5\times10^4$/mL by adding the above working RPMI 1640 medium, sed into 96-well dishes at 150 µl per well, under normal culture conditions mentioned above. Twenty-four hrs after the incubation, the cells were exposed for 48 h at 37° C. with saturated moistures in 5% $CO_2$ incubator to different concentrations of PEITC. Equal volume of the working RPMI 1640 medium was added into the wells of the control group. Each group had four wells. After incubation, discarded the supernatant, added 150 µl D-Hanks per well, washed, discarded the supernatant. After adding 100 µl MTT (0.5 mg/mL), incubated for another 4 hrs. Discarded the supernatant, added 150 µl DMSO, kept at 37° C. for 10 mins. Absorbance was measured at wavelength of 570 nm. The cell growth inhibition was shown in Table 8.

TABLE 8

Inhibitory effects of PEITC on B16 melanoma cells

| Concentrations of PEITC (µmol/L) | Growth Inhibition (%) |
|---|---|
| Blank Control | / |
| 2.5 | 14.46 |
| 5.0 | 27.93 |
| 7.5 | 36.67 |
| 10.0 | 49.23 |
| 12.5 | 58.41 |
| 15.0 | 63.69 |
| 20.0 | 77.35 |
| 30.0 | 89.64 |
| 40.0 | 96.83 |

Results and Discussion:

PEITC showed a significant growth inhibition of B16 mouse melanoma cells in a concentration dependent manner as demonstrated by the data in Table 8 and FIG. 10. The higher concentration, the stronger growth inhibition was seen from the inhibition results. It reached over 96% growth inhibition at concentration of 40 µM. These experiments thus demonstrated that PEITC was effective against B16 melanoma proliferation.

Example 12

Inhibitory Effects of PEITC in Xenograft B16 Mouse Melanoma

Materials and Methods

Reagents:

PEITC was the same as Example 2. B16 mouse melanoma cell line was purchased from the Shanghai Institute of Cell Biology, Chinese Academy of Sciences, Shanghai, China. Fetal bovine serum (FBS) was purchased from Shanghai Hua-Mei Biochemical Reagents Company. RPMI 1640 medium was purchased from Gibco. Penicillin and streptomycin were medical products. Sigma Company provided glutamine and Trypan blue. Trypsin was from Amresco. Cyclophosphamide (CTX) for injection was purchased from Jiangsu Hengrui Medicine Co., Ltd. Saline was purchased from Shanghai Changzheng Fumin medicine Tongling Co., Ltd.

Animal:

Healthy male Kunming mice, at age of 4 to 6 weeks, body weight 18 to 22 grams, were purchased from the Animal Center of Nanjing Medical University.

Where "A" represents a long trail and "B" represents a short track.

Figure 11:
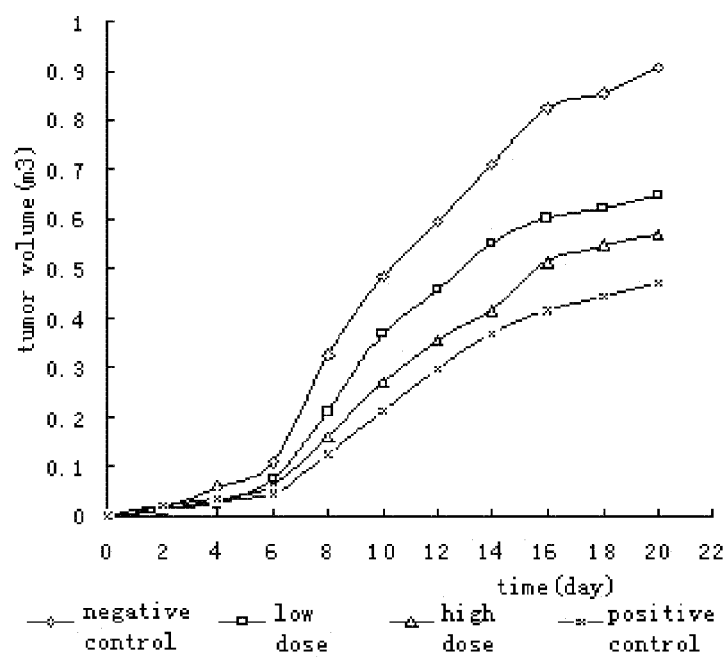
FIG. 11, Effects of phenethyl isothiocyanate (PEITC) on volume enlargement of mouse melanoma cell line by gavage.

A tumor growth curve was obtained by plotting the tumor volume with time (FIG. 11).

TABLE 9

Inhibitory effects of PEITC on xenograft B16 mouse tumor

| Route | Group | No. of Animal | Dose (mg/kg/d) | Changes in Body Weight (g) | Average of Tumor Weight (g) | Inhibition (%) |
|---|---|---|---|---|---|---|
| | Negative Control | 12 | / | 10.32 ± 2.37 | 2.31 ± 0.85 | / |
| O.P. | PEITC (70 mg/kg) | 12 | 70 | 9.78 ± 4.28 | 1.23 ± 0.68* | 39.23 |
| | PEITC (120 mg/kg) | 12 | 120 | 6.34 ± 3.42* | 0.91 ± 0.23**V | 58.54 |
| i.p. | CTX (20 mg/kg) | 12 | 20 | 5.07 ± 2.64* | 0.76 ± 0.41** | 66.23 |

*$P < 0.05$ as compared with the negative control
**$P < 0.01$ as compared with the negative control
V$P > 0.05$ as compared with the positive control Cell Culture, Xenograft B16 Mouse Tumor, and its Passage In Vivo:

B16 mouse melanoma cells were maintained in RPMI 1640 medium containing 10% FBS, 1% 200 mmol/L glutamine, supplemented with 100 U/ml Penicillin and 100 U/ml streptomycin at 37° C. with saturated moistures in 5% $CO_2$ incubator. Adherent cells were digested by 0.25% trypsin for passaging. The B16 mouse melanoma cells at exponential growth phase were suspended in PBS. The cell viability was examined using trepan blue exclusion method to ensure the viability above 98%. Adjusted the suspension to a cell concentration of approximately $1 \times 10^7$/ml. 0.2 ml of the suspension were transplanted subcutaneously into right axillary subcutis for passaging.

Treatment of Xenograft B16 Tumor with PEITC:

Under sterile condition the xenograft B16 mouse tumor in mice was stripped from axillary subcutis. After cutting by scissors, the tumor with saline (1:3) was ground in a glass homogenizer. Monocell suspension was made with saline. The cell viability was examined using trepan blue exclusion method to ensure the viability above 98%. Then adjusted the suspension to a cell density of approximately $1 \times 10^7$/ml with saline. 0.2 ml were transplanted subcutaneously into right axillary subcutis of each mouse. After transplanting, randomly divided the mouse into 5 groups, 12 each.

Started from the next day the animals were treated with or without tested article or control articles once a day for 15 days as follows: two groups were given two different doses of PEITC composition (70 and 120 mg/kg of PEITC, the API, composition as described in Example 13-16) orally by gavage; one group was served as negative control in which animals were given saline only by gavage; another group was served as positive control in which animals were given 20 mg/kg of cyclophosphamide via i.p. Twenty-four hours after the last administration, the animals were euthanized. Tumors were taken out, sizes and weights were measured, and the percent of inhibitions were calculated. The data were shown in Table 9.

Measurement of Tumor Growth Curve:

Tumor volume was measured according to the method described in the official book of Ministry of Health, Drug Council "Principals of Preclinicl Research of New Drug (Western Medicine)". The measurement began at day 4 after the tumor transplantation. The long trail (A) and short track (B) were measured with a vernier caliper, and repeated 3 times for each measurement. The tumor volume was then calculated by the following equation:

$$V = \pi/6[(A+B)/2]^3$$

Results and Discussion:

(1) Compared with the negative control, treatment of xenograft B16 mouse tumor with PEITC by gavage achieved significant anticancer activities ($P<0.05$) as shown in Table 9. Also the anticancer efficacy of PEITC was dose-dependent under the test condition. There is no significant difference ($P>0.05$) between the 58.54% inhibition on xenograft B16 mouse tumor with PEITC and 66.23% inhibition on xenograft B16 mouse tumor with cyclophosphamide (CTX). PEITC is effective via oral administration, thus it is more convenient to patients than the CTX via injection.

(2) FIG. 11 shows that tumor volume is parallel very well with the tumor weight reduction when the tumor volume growth curves is used as the indication for the tumor inhibition. The results confirmed that the PEITC via gavage inhibited the xenograft B16 mouse melanoma, and the efficacy was dose-dependent.

From table 9 and FIG. 11, conclusion can be summarized: PEITC shows anticancer activities on the xenograft B16 mouse melanoma Since melanoma is the most harmful skin cancer in human, our observations in this invention demonstrated that PEITC is effective against the xenograft B16 mouse melanoma, it is reasonable to assume that PEITC will be effective against human skin cancer.

Example 13

Studies of Different Formulations of PEITC

In this invention, we widely, deeply and rationally screened varieties of surfactants, lipid ingredients, and other excipients in order to formulate a better stable and bioavailable isothiocyanate composition for pharmaceutical products and dietary supplements. The in vivo study demonstrated that these compositions have effective inhibition on benign prostatic hyperplasia, prostatitis and skin cancer.

In this invention, the ingredients of the composition for pharmaceutical products and dietary supplements include:
  (a) natural or synthetic isothiocyanates as API;
  (b) surfactants or solubilizing agent: The surfactant used in this invention was to emulsify or enhance solubility of isothiocyanates. Since a surfactant contains both hydrophilic and lipophilic groups, it can surround the API molecules, thus to emulsify and enhance solubility of API and increase their stability;
  (c) lipid ingredients to be used as diluents or a cosolvent;
  (d) antioxidants: to prevent oxidation damage;

(e) other excipients: such as absorbent, diluent, lubricant, binder, disintegrant, solvent, covering and coating material etc. Application of these components in this patent would allow us to make different kinds of formulations like tablets, granules, pills, lyophilized powers, solutions, emulsion, injections, pastes, films, suppositories, sprays, implants and all other available dosage forms.

All formulations in this invention containing PEITC are used as pharmaceutical products or dietary supplements, which are effective against benign prostatic hyperplasia, prostatitis and skin cancer.

Example 13-1

| | |
|---|---|
| 4-sulfophenylisothiocyanate (SPITC) | 10 mg |
| Microcrystalline cellulose (PH102) | 90 mg |
| Anhydrous lactose | 150 mg |
| Colloidal silicon dioxide | 2 mg |

Procedure:

Weighed formulation amount of 4-sulfophenylisothiocyanate, added proportional amount of microcrystalline cellulose (PH102) and anhydrous lactose on the basis of contour incremental principle. Then added colloidal silicon dioxide, mixed evenly, and directly compressed to make tablets.

4-sulfophenylisothiocyanate is a power with an excellent dispersive property. Due to the relative low amount of 4-sulfophenylisothiocyanate in this formulation, microcrystalline cellulose and anhydrous lactose have been used as diluents and directly compressed to tablets.

Example 13-2

| | |
|---|---|
| 4-sulfophenylisothiocyanate(SPITC) | 10 mg |
| Starlac | 288 mg |
| Magnesium stearate | 2 mg |

Procedure:

Mix starlac with 4-sulfophenylisothiocyanate for 5 min. After adding magnesium stearate, mix for additional 5 min, Compress the mixture directly to make the tablets.

Since the starch is inside and lactose outside, the starlac has excellent anti-moisture property. Based on this character, we choose satrlac as diluents in this formulation and compress directly to make tablets.

Example 13-3

| | |
|---|---|
| Phenethyl isothiocyanate (PEITC) | 2.5 mg |
| Medium chain triglyceride | 350 mg |

Procedure:

Phenethyl isothiocyanate (PEITC) was added to medium chain triglycerides and mixed evenly. The mixture was then used to prepare for soft capsules or hard capsules.

Due to an almost water insoluble liquid, formulations are limited for phenethyl isothiocyanate. In the current formulation, the medium chain triglyceride with relative short carbon chain is used because of its good dispersive nature to keep uniform and stability.

Example 13-4

| | |
|---|---|
| Benzyl isothiocyanate (BITC) | 2.5 mg |
| Soybean oil | 350 mg |

Procedure:

Benzyl isothiocyanate (BITC) was added to soybean oil and stirred to mix evenly. The mixture was then used to fill soft capsules or hard capsules.

As compared with Example 13-3, in this formulation, soybean oil was used instead of medium chain triglyceride since soybean oil is easy to obtain with lower price. However soybean oil contains long chain carbon, it may affect the absorption of the API.

Example 13-5

| | |
|---|---|
| Phenethyl isothiocyanate (PEITC) | 2.5 mg |
| Vitamin E polyethylene glycol succinate | 125 mg |

Procedure:

Phenethyl isothiocyanate and vitamin E polyethylene glycol succinate were heated at 60° C. to melt down, and then mixed evenly. The mixture was used to fill hard capsules.

Vitamin E polyethylene glycol succinate is en excellent surfactant; it significant increases dissolution rate of the API when it is used as an excipient. However, Vitamin E polyethylene glycol succinate contains biological active alpha-tocopherol, thus, the potential side effects in this formulation needs to be evaluated.

Example 13-6

| | |
|---|---|
| Phenethyl isothiocyanate (PEITC) | 2.5 mg |
| Polyoxyethylene (40) monostearate | 25 mg |

Procedure:

Phenethyl isothiocyanate and polyoxyethylene (40) monostearate were heated at 60° C. to melt down, and then mixed evenly. The mixture was then used to fill hard capsules of PEITC.

Polyoxyethylene (40) monostearate is one of classic surfactants used as a pharmacopeia listed excipient, and has no potential side effects of biological activity as vitamin E polyethylene glycol succinate. As confirmed in this invention, this formulation exhibited better dissolution rate and stability.

Example 13-7

| | |
|---|---|
| Benzyl isothiocyanate (BITC) | 50 mg |
| Polyethylene glycol 6000 | 300 mg |
| Polyoxyethylene (40) monostearate | 1200 mg |

Procedure:

Polyoxyethylene (40) monostearate was heated on heater with magnetic stirrer to melt down; benzyl isothiocyanate (BITC) was then added and mixed evenly. The mixture was kept warm at 60° C. until no air bubbles, and dropped into coolant dimethyl silicone. The BITC dropping pills were then obtained.

Example 13-8

Dropping Pill Recipe

| Phenethyl isothiocyanate (PEITC) | 50 mg |
|---|---|
| Polyethylene glycol 6000 | 450 mg |
| Polyoxyethylene (40) monostearate | 1050 mg |

Coating Recipe

| Eudragit E100 | 100 mg |
|---|---|
| Acetone | 1420 mg |
| Talc/magnesium stearate | 50 mg |
| Polyethylene glycol 6000(pass 80 mesh) | 10 mg |
| $H_2O$ | 20 mg |

Procedure:

Suitable amount of polyethylene glycol 6000 (PEG6000) and polyoxyethylene (40) monostearate indicated in above dropping pill recipe were heated to melt down, PEITC was then added and mixed evenly. The mixture was kept at a 70° C. water bath until no air bubble. And then dropped the mixture into the coolant dimethyl silicone to form PEITC dropping pills.

Suitable amount of talc/magnesium stearate indicated in the coating recipe above was added to acetone and mixed evenly (acetone mixture). Suitable amount of PEG 6000 was dissolved in suitable amount $H_2O$ indicated in the coating recipe above (PEG solution). The acetone mixture was then mixed evenly with PEG 6000 solution and dispensed with a ball mill to make an uniform suspension (PEG suspension). Suitable amount of Eudragit E100 was dissolved in acetone to obtain 12.5% Eudragit acetone solution. Add this solution to the PEG suspension. Adjust the newly formed mixture with acetone to obtain a 8-10% coating solution.

The PEITC dropping pills were placed into coated pot, and the coating solution was sprayed while the pot was rotated, and the pills coated. PEITC capsule was then obtained by filling empty capsules with suitable amount of coated PEITC dropping pills.

Example 13-9

| Phenethyl isothiocyanate (PEITC) | 25 mg |
|---|---|
| Vitamin E polyethylene glycol succinate | 50 mg |
| Poloxamer F-127 | 50 mg |
| Sorbitol | 75 mg |
| Porous starch | 193 mg |
| Microcrystalline cellulose PH101 | 392 mg |
| 10% polyvinylpyrrolidone K30 alcohol solution | 0.5 ml |
| Talc | 15 mg |

Procedure:

Suitable amount of PEITC, vitamin E polyethylene glycol succinate and poloxamer F-127 specified in recipe above were heated to melt down. The sorbitol, porous starch and microcrystalline cellulose PH101 was added, stirred until mixing evenly. 10% polyvinylpyrrolidone K30 alcohol solution was added while stirring to make granules, passed sieve, and dried at a 60° C. oven for 30 min to get dry granules. The talc was then added, stirred until uniform and hard capsules were filled.

Example 13-10

| Benzyl isothiocyanate (BITC) | 2.5 mg |
|---|---|
| Medium-chain triglycerides | 2 mg |
| Tween 80 | 25 mg |

Procedure:

Suitable amount of BITC, medium-chain triglycerides and Tween 80 specified in above recipe were mixed evenly, and the mixture was used to fill hard capsules. In order to improve the dissolution rate of BITC, add the surfactant Tween 80 to the recipe in example 13-3. Experimental data showed that the dissolution rate was significantly improved.

Example 13-11

| Phenethyl isothiocyanate (PEITC) | 2.5 mg |
|---|---|
| Medium-chain triglycerides | 2 mg |
| Polyoxyethylene (40) monostearate | 25 mg |

Procedure:

Suitable amount of polyoxyethylene (40) monostearate specified in above recipe were melted at 60° C., mixed well with PEITC and medium-chain triglycerides. The mixture was used to fill hard gel capsules.

The products made according to this formulation were used for experiments described in Example 5 (Therapeutic Effects of PEITC on BPH: Test One) Example 6 (Therapeutic Effects of PEITC on BPH: Test Two) and Example 7 (Therapeutic Effects of PEITC on Non-bacterial Prostatitis). Satisfactory results were obtained from all of these experiments.

The design of formulations of PEITC were restricted due to its poor solubility in aqueous solution. Referring example 13-3 and example 13-6, both medium-chain triglycerides and polyoxyethylene (40) monostearate were used at the same time in this formulation. Polyoxyethylene (40) monostearate has been widely used as the surfactant in the formulations of poor solubility API. Our experiment support the conclusion that polyoxyethylene (40) monostearate enhances the solubility of API otherwise it would be difficulty to dissolve. Experiments both in vitro and in vivo showed that this formulation was not only rather stable, but also had a better dissolution rate. Thus, we conclude that this formulation may be proven to be one of the valuable formulations of PEITC in clinical application.

Example 13-12

| | |
|---|---|
| Allyl isothiocyanate (AITC) | 2.5 mg |
| Medium-chain triglycerides | 320 mg |
| Polyoxyethylene (40) monostearate | 40 mg |

Procedure:

Suitable amount of allyl isothiocyanate (AITC), medium-chain triglycerides, and Polyoxyethylene (40) monostearate specified in above recipe were heated to melt, stirred and mixed evenly. The mixture was then pressed to make soft capsules.

Since allyl isothiocyanate also is a liquid with poor solubility in water, the same principle described in Example 13-11 was applied. To increase the stability of AITC, a slight higher percentage of medium-chain triglycerides was used in this formulation.

Example 13-13

| | |
|---|---|
| Phenethyl isothiocyanate (PEITC) | 50 mg |
| Stearic acid | 150 mg |
| Polyoxyethylene (40) monostearate | 1350 mg |

Procedure:

Stearic acid and polyoxyethylene (40) monostearate was melted by heating on a heater with magnetic stirrer, the PEITC was then added while stirring. The mixture was kept at 60° C. in a water bath until no air bubble, dropped into the coolant dimethyl silicone to obtain dropping pills of PEITC.

This formulation was also an improvement of the formulation of Example 13-11. Compared with recipe in Example 13-11, stearic acid was used to replace medium-chain triglycerides. The idea is that stearic acid is structurally similar to polyoxyethylene (40) monostearate, thus a better compatibility can be expected when these two are used together.

Example 13-14

| | |
|---|---|
| Benzyl isothiocyanate (BITC) | 50 mg |
| Stearic acid | 300 mg |
| Polyoxyethylene (40) monostearate | 1200 mg |

Procedure:

Stearic acid and polyoxyethylene (40) monostearate was melted by heating on a heater with magnetic stirrer, the BITC was then added while stirring. The mixture was kept at 60° C. in a water bath until no air bubble, dropped into the coolant dimethyl silicone was to obtain dropping pills of BITC.

Compared with example 13-13, in this formulation the ratio of stearic acid to the API and polyoxyethylene (40) monostearate was increased, which increased melting point of the mixture and made it easier to form dropping pills besides the change of API from PEITC to BITC.

Example 13-15

| | |
|---|---|
| Benzyl isothiocyanate (BITC) | 25 mg |
| Medium-chain triglycerides | 20 mg |
| Polyoxyethylene (40) monostearate | 100 mg |
| Vitamin E polyethylene glycol succinate | 125 mg |

Procedure:

BITC, medium-chain triglycerides, polyoxyethylene (40) monostearate, and vitamin E polyethylene glycol succinate were melted by heating to 60° C. on a heater. After mixing evenly, fill the mixture into hard capsules.

Example 13-16

| | |
|---|---|
| Phenethyl isothiocyanate (PEITC) | 25 mg |
| Medium-chain triglycerides | 20 mg |
| Polyoxyethylene (40) monostearate | 75 mg |
| Polyoxyethylene (35) castor oil | 50 mg |

Procedure:

PEITC, medium-chain triglycerides, polyoxyethylene (40) monostearate, and polyoxyethylene (35) castor oil were melted by heating to 60° C. on a heater. After mixing evenly, fill the mixture into capsules.

This formulation was modified from the formulation of Example 13-11, in which polyoxyethylene (35) castor oil was added to improve the solubility of API in aqueous phase.

Example 13-17

| | |
|---|---|
| Benzyl isothiocyanate (BITC) | 25 mg |
| Cottonseed oil | 20 mg |
| Polyoxyethylene (40) monostearate | 250 mg |
| Polyoxyethylene (35) castor oil | 50 mg |

Procedure:

BITC, cottonseed oil, polyoxyethylene (40) monostearate, and polyoxyethylene (35) castor oil were melted by heating to 60° C. on a heater. After mixing evenly, fill the mixture into hard gel capsules.

Example 13-18

| | |
|---|---|
| Phenethyl isothiocyanate (PEITC) | 100 mg |
| Medium-chain triglycerides | 90 mg |
| Polyoxyethylene (40) monostearate | 250 mg |
| Polyethylene glycol 6000 | 2500 mg |

Procedure:

Polyethylene glycol 6000 and polyoxyethylene (40) monostearate were heated to melt on a heater with magnetic stirrer. PEITC and medium-chain triglycerides were then added and mixed. The mixture was kept at 70° C. in a water bath until no air bubble, dropped into the coolant dimethyl silicone to obtain dropping pills of PEITC. The remaining dimethyl silicone on the surface of dropping pills was washed away with anhydrous ether. Fill the mixture into capsules after the ether was evaporated.

Compared with the formulation of Example 13-11, the melting point of this formulation was increased as a result of the addition of higher melting point polyethylene glycol 6000, which made dropping pills easy to form.

Example 13-19

| | |
|---|---|
| Phenethyl isothiocyanate (PEITC) | 25 mg |
| Vitamin E (tocopherol) | 25 mg |
| Vitamin E polyethylene glycol succinate | 75 mg |
| Polyethylene glycol 400 | 25 mg |

Procedure:

Polyethylene glycol 4000 and vitamin E polyethylene glycol succinate were warmed up to 60° C. on a water bath, PEITC and tocopherol were then added, mixed evenly, and filled into hard gel capsules when the mixture was warm.

In this formulation, vitamin E polyethylene glycol succinate was used as surfactant. Since vitamin E polyethylene glycol succinate consists of α-tocopherol and polyethylene glycol, on the basis of the principle of similar structure, similar dissolvability the affinity among these components in this formulation would be better. However, the shortage of this formulation is that both vitamin E polyethylene glycol succinate and vitamin E themselves have biological activities, which may result in positive or negative effects to specific diseases.

Example 13-20

| | |
|---|---|
| Phenethyl isothiocyanate (PEITC) | 2.5 mg |
| Medium-chain triglycerides | 2.0 mg |
| Polyoxyethylene (40) monostearate | 25 mg |
| Sodium carboxymethyl starch (CMS) | 300 mg |
| Polyethylene glycol 6000 (pass 80 mesh) | 10 mg |

Procedure:

PEITC, polyoxyethylene (40) monostearate and medium-chain triglycerides were warmed up to melt, sodium carboxymethyl starch (CMS) was then added, and mixed, followed by the addition of polyethylene glycol 6000 powder. After mixing evenly, fill the mixture into capsules.

Sodium carboxymethyl starch (CMS) is an excellent binder. In this formulation we intended to explore whether we could develop a powder formulation containing liquid form of PEITC based on the formulation of example 13-11.

Example 13-21

Tablet Recipe:

| | |
|---|---|
| 4-sulfophenylisothiocyanate (SPITC) | 10 mg |
| β-cyclodextrin (Kleptose DC) | 240 mg |
| Mannitol (Pearlitol SD200) | 240 mg |
| Magnesium Stearte | 10 mg |

Coating Recipe:

| | |
|---|---|
| Hydroxypropylmethyl cellulose E15 | 0.4 mg |
| Hydroxypropyl cellulose EF | 0.4 mg |
| Polyethylene glycol 400 | 0.08 mg |
| Potassium sorbate | 0.014 mg |
| $H_2O$ | 10 mg |

Procedure:

4-sulfophenylisothiocyanate (SPITC), Kleptose DC and Pearlitol SD200 were added into the turbine agitator and agitated for 10 mins. Magnesium Stearte was then added, and agitated for additional 5 mins. The mixing powder was directly compressed into tablets.

Adequate amount of water was warmed up, and added with hydroxypropylmethyl cellulose E15, hydroxypropyl cellulose EF, polyethylene glycol 400 and potassium sorbate while stirring to obtain coating solution. The tablets obtained above were then placed into a coating pan. The coated tablets were obtained by spraying the coating solution on the tablets while rotating.

Example 13-22

| | |
|---|---|
| Phenethyl isothiocyanate (PEITC) | 25 mg |
| Polyoxyethylene (40) hydrogenated castor oil | 225 mg |

Procedure:

PEITC was mixed with polyoxyethylene (40) hydrogenated castor oil evenly, and then filled into hard gel capsules at 40° C.

Polyoxyethylene (40) hydrogenated castor oil is one of popular solubilizing agents for API with poor solubility recently. In addition to its efficiency, its semi-solid nature under room temperature makes it as an ideal excipient for semi-solid pharmaceutical preparations.

Example 13-23

| | |
|---|---|
| Phenethyl isothiocyanate (PEITC) | 25 mg |
| Polyoxyethylene (35) castor oil | 200 mg |
| Tween 80 | 75 mg |
| Vitamin E (tocopherol) | 5 mg |

Procedure:

PEITC was evenly mixed with polyoxyethylene (35) castor oil, Tween 80, and vitamin E (tocopherol), and the mixture was then filled into soft gel capsules.

Example 14

Stability Testing of Isothiocyanate Compositions

Instruments:

S.C.101 electric thermostat dry oven, Zhejing Jiaxing Xingsheng Electrical Heating Instrument Factory; METTLER AE 100 electronic balance, Ruishimeitele, Swiss; Agilent 1100 HPLC, Agilent, USA.

Method:

Suitable amount of API (isothiocyanates, as control) and compositions were placed into clean vials, and sealed with rubber stoppers plus aluminum caps. All samples were stored at 60° C., and then assayed by a validated HPLC method at time day 0, day 5, and day 10.

Results:

The test results were summarized in Table 10.

TABLE 10

Partial results of stability testing of isothiocyanate formulations

| Compositions in Example | Under 60° C. for 10 days (API %) |
|---|---|
| Control (exampled by PEITC) | 95.2 |
| 13-3 | 98.8 |
| 13-4 | 96.9 |
| 13-6 | 95.3 |
| 13-11 | 99.4 |
| 13-12 | 99.0 |
| 13-21 | 95.4 |

Discussion:

The results shown above indicated that compositions composing of isothiocyanates and oil components (example 13-3, 13-4) above was more stable than the API themselves. In addition, stability of isothiocyanates in the mixtures of oil (corn oil or medium-chain triglycerides) and polyoxyethylene (40) monostearate at different ratios also improved as compared with themselves alone. These observations suggest that adequate oil excipients and surfactant polyoxyethylene (40) monostearate may increase the stability of isothiocyanates although the mechanisms need to be defined.

Example 15

Testing of in Vitro Dissolution of Isothiocyanate Compositions

Materials and Methods:

Medicine: Isothiocyanates compositions were the same as described in example 13.

Instruments: Dissolution tester: Smart Drug Dissolution Instrument, Tianjin University Precision Instrument Factory; HPLC: Agilent 1100 HPLC, Agilent, USA.

Dissolution Measurement: Dissolution rates of the compositions were measured according to the procedures described in the Chinese Pharmacopeia 2005, Appendix XC, Method 2: Paddle Determination. Briefly, samples are added into 500 ml of de-aired, and deionized water which is kept at 37±0.5° C. for 45 min while the paddle rotates at 200 r/min. Take samples and let the sample be passed through the 0.8 μm filter membrane, and analyzed by HPLC. The dissolution rate was then calculated.

Results:

The results were shown in Table 11.

TABLE 11

Partial results of dissolution rate of isothiocyanate formulations

| Compositions in Example | Dissolution Rate % |
|---|---|
| Control (exampled by PEITC) | 0 |
| 13-7 | 73.9 |
| 13-8 | 62.9 |
| 13-11 | 65.0 |
| 13-13 | 57.3 |
| 13-14 | 16.8 |
| 13-15 | 72.9 |
| 13-16 | 70.1 |
| 13-19 | 52.0 |
| 13-22 | 86.6 |
| 13-23 | 77.2 |

Experiment Discussion: The data shown in Table 11 indicated that the dissolution rate of isothiocyanate itself was nearly zero. However, when it was formulated with various oil excipients plus surfactant(s), the dissolution rate of isothiocyanate was improved, and the oil components somehow were negatively related to the dissolution from the experiment results.

On the basis of stability testing results shown in example 14 and dissolution testing data in example 15, we conclude that the stabilities of isothiocynates formulated with oil or formulated with both oil and surfactant(s) are acceptable. On the other hand the dissolution rates are better in compositions containing oil plus surfactant(s) than in compositions containing oil only. Moreover, the pharmacodynamic studies described in example 5, 6, 7, 10, and 12 using compositions containing excipients of both oil and surfactants also showed significantly therapeutic activities in preventing and treating benign prostates hyperlasia, prostatitis, prostate cancer and skin cancer.

Discussion:

Prostatic disease is one of major diseases that significantly impact the quality of men's life, particularly elder men, and the incidence of the disease is increasing worldwide. Drug treatment is still the main methodology for the treatment of the disease at present. However, current drugs for prostatic diseases have unwanted or unfavorable effects. For example, medications derived from steroid hormones have some side effects of steroids. Other drugs are either lack of knowledge of API, unclear mechanism, or their therapeutic efficacies are not satisfactory. Thus, to develop new pharmaceutical products, dietary supplements or cosmetic products with ideal efficacy and safety profiles for the treatment and prevention of various prostatic diseases is warranted.

The major risk factor of skin cancer is UV light which mainly comes from the exposure of sun, thus everyone, no matter his/her race, skin property, age, occupation, and residential location, has risk to develop skin cancer. In recent years the incidence of skin cancer is constantly increasing as a result of more sun light exposure due to the popularity of outdoor activities which is one of the results of uprising living standard. While effective drug is limited, it will have important value on the medical application to develop a pharmaceutical product or dietary supplement for the treatment and prevention of skin cancer.

In this invention, we demonstrated, via test data obtained from various in vitro and in vivo models, that isothiocyanates which had the isothiocyanic function group, included but not limited to phenethyl isothiocyanate (PEITC), benzyl isothiocyanate (BITC), allyl isothiocyanate (AITC), and 4-sulfophenylisothiocyanate (SPITC), and N-acetylcysteine conjugate of phenethyl isothiocyanate (PEITC-NAC) etc., effectively treated and/or prevented prostatic diseases including but not limited to benign prostatic hyperplasia, prostatitis, and prostate cancer. On the basis of above findings, we further studied molecular mechanisms by which isothiocyanates effectively treat and prevent prostatic diseases. We showed that isothiocyanates induce expression of phase II detoxification enzyme GSTP1. The increased levels and activity of GSTP1 protects cells from assaults of endogenous and exogenous toxin, thereby treat and prevent benign prostatic hyperplasia, prostatitis, prevent pathogenesis of the prostate. In addition, partial isothiocyanates, such as PEITC effectively repress expressions of the androgen receptor (AR), transcription factor Sp1, an upstream gene of AR, and prostate specific antigen (PSA), a downstream gene of the AR to inhibit the pathogenesis of benign prostatic hyperplasic and prostate cancer. Moreover, it is worth to note that APIs in this patent are orally effective, thus they are convenient to be administered, and easier to compliance. This characteristic is of a great advantage of patients with chronic prostate diseases for which long-term therapy is needed. In this invention, we also provided evidence that PEITC was effective against skin diseases, including, but not limited to skin cancer. We showed that PEITC effectively inhibited growth of B16 mouse melanoma cells by using both in vitro and in vivo models. Our data indicated that PEITC has wide anticancer spectrum. Many scientists have demonstrated that PEITC is an effective agent for the chemoprevention of various cancers, and now in this invention, we further demonstrated the efficacy of PEITC for the treatment and prevention of various prostate diseases. Obviously, our invention creates important transnational medical applications of isothiocyanates.

In order to transform the pharmaceutical active isothiocyanates into valuable products, extensive study has been made on compositions and manufacturing process. Compositions of pharmaceutical products and dietary supplements using isothiocynates as API are included in this patent. Most of those compositions have been shown to have ideal dissolution rate and stability. Since the effective dose of API is low, thus, we can expect that the pharmaceutical products or dietary supplements, not only have low side effects, but the cost of the production will be also low, which will reduce financial burden of consumers. The manufacture procedures of the API have been developed in this invention. We provided the processes to extract the API from vegetables, or to synthesize them. As described above, this invention provided a novel, applicable and prospective product.

APPLICATION POSSIBILITY IN INDUSTRY

Considering the poor aqueous solubility of majority of isothiocyanates or their derivatives, including PEITC, we provide various applicable formulations by using pharmaceutical excipients to disperse the API first, thus enhance their bioavailability based on the needs of different administration. Those formulations produced ideal therapeutic effects at low API doses and reduced side effects. Pharmacodynamic studies using various animal models showed that the efficacy of those formulations were equal, might in some way better than, to Proscar or GENURIN respectively. It was a breakthrough to such chronic diseases which need long term drug therapy as BPH and prostatitis. The animal studies in this invention proved that isothiocyanates, especially PEITC, were effective against BPH and non-bacterial prostatitis at a low dosage. Besides, the in vitro and in vivo studies also showed that isothiocyanates, especially PEITC, which had inhibitory effect on skin cancer, can be used as the drug for the prevention and treatment of the skin cancer. This invention further demonstrated that various isothiocyanates and their derivatives can induce Phase II detoxification enzyme, i.e. glutathione S-transferase (GSTP1); isothiocyanates, their derivatives, and metabolites (except 4-sulfophenylisothiocyanate (SPITC), its derivatives, and metabolites) are able to inhibit expressions of androgen receptor (AR), AR upstream gene Sp1, and AR downstream gene, prostate specific antigen (PSA) in the human prostate cancer cell line LNCaP by molecular biological methods, In this way, the patent provides the molecule mechanism of inhibiting benign prostates hyperplasia and prostatitis by isothiocyanates, their derivatives and metabolites. Therefore from this invention it can be expected that isothiocyanates, especially PEITC, and their derivatives have wide application possibility which may be used as pharmaceutical products, dietary supplements and cosmetic products for the treatment and/or prevention of prostatic diseases and skin cancers.

The invention claimed is:

1. A method for the treatment of prostatitis in a subject, comprising: administrating, to the subject, a composition comprising an effective amount of at least one selected from the group consisting of an isothiocyanate compound, a derivative of an isothiocyanate compound, and a metabolite of an isothiocyanate compound,
   wherein the isothiocyanate compound is at least one selected from the group consisting of:
   benzyl isothiocyanate (BITC) isothiocyanate (PEITC), allyl isothiocyanate (AITC) and 4-sulfophenylisothiocyanate which have the following formulas (1), (2), (3), and (4), respectively;

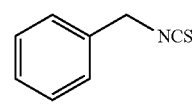

(1)

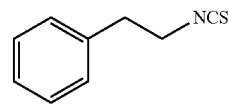

(2)

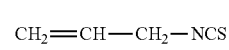

(3)

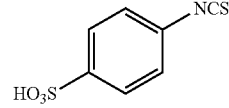

(4)

and wherein each of said derivative and metabolite is at least one selected from the group consisting of a glutathione-conjugate, a cysteinyl glycine-conjugate, a cysteinyl-conjugate, and an N-acetylcysteine-conjugate.

2. The method of claim 1, wherein the effective amount is an amount effective for inducing the expression of glutathione S-transferase (GSTP1) gene in prostate cells.

3. The method of claim 1, wherein the effective amount is an amount effective for inhibiting the expressions of (i) androgen receptor (AR), (ii) transcription factor Sp1, the upstream gene of androgen receptor (AR), and (iii) prostate specific antigen (PSA), the downstream gene of AR.

4. The method of claim 1, wherein each of the derivative and the metabolite is at least one selected from the group consisting of: N-acetylcysteine conjugate of benzyl isothiocyanate (BITC-NAC), N-acetylcysteine conjugate of phenethyl isothiocyanate (PEITC-NAC), N-acetylcysteine conjugate of allyl isothiocyanate (AITC-NAC), and N-acetylcysteine conjugate of 4-sulfophenylisothiocyanate (SPITC-NAC), which have the following formulas (5), (6), (7), and (8) respectively:

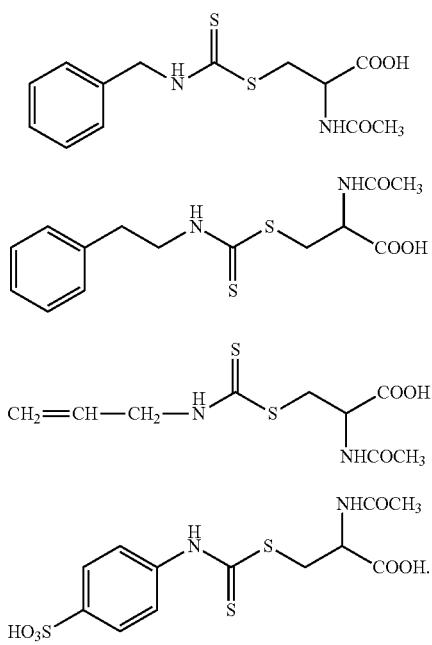

5. The method of claim 1, wherein the isothiocyanate compound, the derivative, or the metabolite is used alone or used as a formulation with excipients.

6. The method of claim 5, wherein the formulation is at least one selected from the group consisting of a pharmaceutical product, dietary supplement, food, and cosmetic product.

7. The method of claim 1, wherein the composition contains the following ingredients:

(a) an active pharmaceutical ingredient(API), wherein said API is at least one selected from the group consisting of an isothiocyanate compound, a derivative of an isothiocyanate compound, and a metabolite of an isothiocyanate compound, wherein the isothiocyanate compound is at least one selected from the group consisting of: benzyl isothiocyanate (BITC), phenethyl isothiocyanate (PEITC), allyl isothiocyanate (AITC), and 4-sulfophenylisothiocyanate (SPITC), which have the following formulas (1), (2), (3), and (4) respectively;

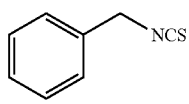

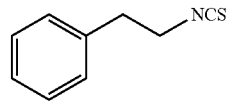

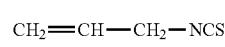

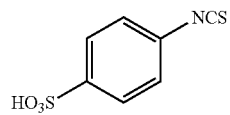

and wherein said derivative and metabolite is at least one selected from the group consisting of a glutathione-conjugate, a cysteinyl glycine-conjugate, a cysteinyl-conjugate, and an N-acetylcysteine-conjugate, and (b) a pharmaceutically acceptable carrier for the API, wherein said carrier is at least one selected from the group consisting of a surfactant, a solubilizing agent, an oil ingredient, and an antioxidant;

wherein the surfactant is at least one selected from the group consisting of polyoxyethylene lauryl ether, polyoxyethylene glycol monostearate, vitamin E polyethylene glycol succinate, polyoxyethylene castor oil, polyoxyethylene hydrogenated castor oil, poloxamer, and a polysorbate;

wherein the solubilizing agent is at least one selected from the group consisting of polyvinylpyrrolidone K17, K25, K30, or K90; and polyethylene glycol 400, 4000, or 6000;

wherein the oil ingredient is at least one selected from the group consisting of fatty acids, triglyceride, monoglyceride, diglyceride, soybean oil, corn oil, peanut oil, stearic acid, palmitic acid, palm oil, sunflower oil, olive oil, coconut oil, sesame oil, cottonseed oil, canola oil, oleic acid, linoleic acid, medium-chain triglycerides, glyceryl monooctadecanoate, glyceryl monoacetate, glyceryl diacetate, and glyceryl triacetate; and wherein the antioxidant is a water-soluble antioxidant or a fat-soluble antioxidant, and is at least one selected from the group consisting of vitamin C, vitamin C palmitate, propyl gallate, tocopherol, tert-butylated-p-hydroxyanisole, and 2,6-di-tert-butyl-p-methylphenol.

8. The method of claim 7, wherein the composition is at least one selected from the group consisting of a tablet, a capsule, a pill, a powder for injection, an injection, a lyophilized powder, an ointment, a suppository, a cream, a film, an emulsion, a spray, and an implant.

9. The method of claim 7, wherein the composition is a pharmaceutical product or a dietary supplement.

10. The method of claim 7, wherein the composition is administered orally, intravenously, muscularly, subcutaneously, intracavitaryly, sublingually, anally, or topically.

11. The method of claim 1, wherein the composition is administrated alone or in a combined therapy.

12. The method of claim 11, wherein the combined therapy is at least one therapy selected from the group consisting of surgery, radiation, gene therapy, and biologics.

* * * * *